US010936746B2

(12) United States Patent
Farlow et al.

(10) Patent No.: US 10,936,746 B2
(45) Date of Patent: Mar. 2, 2021

(54) METHOD AND SYSTEM FOR MANIPULATING AND COMMUNICATING GENETIC CONSTRUCTS INDEPENDENT OF THEIR GENETIC SEQUENCE

(71) Applicant: SEROTINY, INC., San Francisco, CA (US)

(72) Inventors: Justin Farlow, San Francisco, CA (US); Colin Farlow, Portland, OR (US)

(73) Assignee: SEROTINY, INC., San Francisco, CA (US)

( * ) Notice: Subject to any disclaimer, the term of this patent is extended or adjusted under 35 U.S.C. 154(b) by 212 days.

(21) Appl. No.: 15/838,283

(22) Filed: Dec. 11, 2017

(65) Prior Publication Data
US 2018/0218172 A1 Aug. 2, 2018

Related U.S. Application Data

(60) Provisional application No. 62/437,608, filed on Dec. 21, 2016.

(51) Int. Cl.
*G06F 21/62* (2013.01)
*G06F 21/60* (2013.01)
(Continued)

(52) U.S. Cl.
CPC ...... *G06F 21/6245* (2013.01); *G06F 16/2474* (2019.01); *G06F 21/602* (2013.01); *G16B 50/00* (2019.02)

(58) Field of Classification Search
CPC .............. G06F 21/6245; G06F 16/2474; G06F 21/602; G16B 50/00
See application file for complete search history.

(56) References Cited

U.S. PATENT DOCUMENTS

| 2004/0006433 A1* | 1/2004 | Robson | G16B 30/00 |
| | | | 702/20 |
| 2007/0271604 A1* | 11/2007 | Webster | G06F 21/6245 |
| | | | 726/10 |

(Continued)

OTHER PUBLICATIONS

"Biotherapeutic Discovery Platform: custom protein registry for your lab or company," serotiny Website, Available Onine at https://serotiny.bio/notes/applications/car/, Available as Early as May 1, 2017, 5 pages.

*Primary Examiner* — Chau Le
(74) *Attorney, Agent, or Firm* — McCoy Russell LLP

(57) ABSTRACT

Methods and systems are disclosed for genetic manipulation and for securing communication of genetic sequences. In one example, a sequence security system comprises a security device communicatively coupled to a separator module, the separator module comprising a first separator device and a second separator device. The security device may store instructions in non-transitory memory that are executable by a processor to receive a source sequence from the first separator device at a receiving module, receive manipulation instructions from the second separator device at the receiving module, and apply the manipulation instructions to the source sequence to form a target sequence via a transforming module. Thus, the source sequence and the manipulation instructions may be maintained separate from one another until the source sequence and the manipulation instructions are received at the receiving module, for example.

20 Claims, 10 Drawing Sheets

Specification includes a Sequence Listing.

(51) Int. Cl.
    *G06F 16/2458*     (2019.01)
    *G16B 50/00*       (2019.01)

(56) References Cited

U.S. PATENT DOCUMENTS

| | | | |
|---|---|---|---|
| 2008/0077607 A1* | 3/2008 | Gatawood ........... | H03M 7/3084 |
| 2012/0095693 A1* | 4/2012 | Ganeshalingam ...... | G06F 16/22 |
| | | | 702/19 |
| 2012/0236861 A1* | 9/2012 | Ganeshalingam ...... | H04L 45/00 |
| | | | 370/392 |
| 2017/0199962 A1* | 7/2017 | Ganeshalingam ...... | G06F 16/22 |

* cited by examiner

SEQUENCE LISTING

```
<160> NUMBER OF SEQ ID NOS: 7

<210> SEQ ID NO 1
<211> LENGTH: 239
<212> TYPE: PRT
<213> ORGANISM: Artificial Sequence
<220> FEATURE:
<223> OTHER INFORMATION: Enhanced version of Aequorea victoria Green
      Fluorescent Protein

<400> SEQUENCE: 1

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
```

```
                    100                 105                 110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 2

<400> SEQUENCE: 2

000

<210> SEQ ID NO 3
<211> LENGTH: 125
<212> TYPE: PRT
<213> ORGANISM: Artificial Sequence
<220> FEATURE:
<223> OTHER INFORMATION: Similar to Human Histone 2B

<400> SEQUENCE: 3

Pro Glu Pro Ala Lys Ser Ala Pro Ala Pro Lys Lys Gly Ser Lys Lys
1               5                   10                  15

Ala Val Thr Lys Ala Gln Lys Lys Gly Gly Lys Lys Arg Lys Arg Ser
            20                  25                  30

Arg Lys Glu Ser Tyr Ser Ile Tyr Val Tyr Lys Val Leu Lys Gln Val
        35                  40                  45

His Pro Asp Thr Gly Ile Ser Ser Lys Ala Met Gly Ile Met Asn Ser
    50                  55                  60

Phe Val Asn Asp Ile Phe Glu Arg Ile Ala Gly Glu Ala Ser Arg Leu
65                  70                  75                  80

Ala His Tyr Asn Lys Arg Ser Thr Ile Thr Ser Arg Glu Ile Gln Thr
                85                  90                  95

Ala Val Arg Leu Leu Leu Pro Gly Glu Leu Ala Lys His Ala Val Ser
            100                 105                 110

Glu Gly Thr Lys Ala Ile Thr Lys Tyr Thr Ser Ala Lys
        115                 120                 125

<210> SEQ ID NO 4
<211> LENGTH: 365
<212> TYPE: PRT
<213> ORGANISM: Artificial Sequence
<220> FEATURE:
<223> OTHER INFORMATION: Fusion protein of GFP, linker, and human
      Histone 2B

<400> SEQUENCE: 4

Met Val Ser Lys Gly Glu Glu Leu Phe Thr Gly Val Val Pro Ile Leu
```

```
                1               5                   10                  15
        Val Glu Leu Asp Gly Asp Val Asn Gly His Lys Phe Ser Val Ser Gly
                        20                  25                  30

Glu Gly Glu Gly Asp Ala Thr Tyr Gly Lys Leu Thr Leu Lys Phe Ile
                    35                  40                  45

Cys Thr Thr Gly Lys Leu Pro Val Trp Pro Thr Leu Val Thr Thr Leu
                50                  55                  60

Thr Tyr Gly Val Gln Cys Phe Ser Arg Tyr Pro Asp His Met Lys Gln
        65                  70                  75                  80

His Asp Phe Phe Lys Ser Ala Met Pro Glu Gly Tyr Val Gln Glu Arg
                            85                  90                  95

Thr Ile Phe Phe Lys Asp Asp Gly Asn Tyr Lys Thr Arg Ala Glu Val
                        100                 105                 110

Lys Phe Glu Gly Asp Thr Leu Val Asn Arg Ile Glu Leu Lys Gly Ile
                    115                 120                 125

Asp Phe Lys Glu Asp Gly Asn Ile Leu Gly His Lys Leu Glu Tyr Asn
                130                 135                 140

Tyr Asn Ser His Asn Val Tyr Ile Met Ala Asp Lys Gln Lys Asn Gly
        145                 150                 155                 160

Ile Lys Val Asn Phe Lys Ile Arg His Asn Ile Glu Asp Gly Ser Val
                            165                 170                 175

Gln Leu Ala Asp His Tyr Gln Gln Asn Thr Pro Ile Gly Asp Gly Pro
                        180                 185                 190

Val Leu Leu Pro Asp Asn His Tyr Leu Ser Thr Gln Ser Ala Leu Ser
                    195                 200                 205

Lys Asp Pro Asn Glu Lys Arg Asp His Met Val Leu Leu Glu Phe Val
                210                 215                 220

Thr Ala Ala Gly Ile Thr Leu Gly Met Asp Glu Leu Tyr Lys Gly Ser
        225                 230                 235                 240

Pro Glu Pro Ala Lys Ser Ala Pro Ala Pro Lys Lys Gly Ser Lys Lys
                            245                 250                 255

Ala Val Thr Lys Ala Gln Lys Lys Gly Gly Lys Lys Arg Lys Arg Ser
                        260                 265                 270

Arg Lys Glu Ser Tyr Ser Ile Tyr Val Tyr Lys Val Leu Lys Gln Val
                    275                 280                 285

His Pro Asp Thr Gly Ile Ser Ser Lys Ala Met Gly Ile Met Asn Ser
                290                 295                 300

Phe Val Asn Asp Ile Phe Glu Arg Ile Ala Gly Glu Ala Ser Arg Leu
        305                 310                 315                 320

Ala His Tyr Asn Lys Arg Ser Thr Ile Thr Ser Arg Glu Ile Gln Thr
                            325                 330                 335

Ala Val Arg Leu Leu Leu Pro Gly Glu Leu Ala Lys His Ala Val Ser
                        340                 345                 350

Glu Gly Thr Lys Ala Ile Thr Lys Tyr Thr Ser Ala Lys
                    355                 360                 365

<210> SEQ ID NO 5
<211> LENGTH: 239
<212> TYPE: PRT
<213> ORGANISM: Artificial Sequence
<220> FEATURE:
<223> OTHER INFORMATION: Mutation of GFP, S3A

<400> SEQUENCE: 5

Met Val Ala Lys Gly Glu Glu Leu Phe Thr Gly Val Val Pro Ile Leu
```

```
                1               5                  10                 15
        Val Glu Leu Asp Gly Asp Val Asn Gly His Lys Phe Ser Val Ser Gly
                        20                  25                 30
        Glu Gly Glu Gly Asp Ala Thr Tyr Gly Lys Leu Thr Leu Lys Phe Ile
                        35                  40                 45
        Cys Thr Thr Gly Lys Leu Pro Val Pro Trp Pro Thr Leu Val Thr Thr
                50                      55                  60
        Leu Thr Tyr Gly Val Gln Cys Phe Ser Arg Tyr Pro Asp His Met Lys
        65                      70                  75                 80
        Gln His Asp Phe Phe Lys Ser Ala Met Pro Glu Gly Tyr Val Gln Glu
                            85                  90                 95
        Arg Thr Ile Phe Phe Lys Asp Asp Gly Asn Tyr Lys Thr Arg Ala Glu
                        100                 105                110
        Val Lys Phe Glu Gly Asp Thr Leu Val Asn Arg Ile Glu Leu Lys Gly
                        115                 120                125
        Ile Asp Phe Lys Glu Asp Gly Asn Ile Leu Gly His Lys Leu Glu Tyr
                        130                 135                140
        Asn Tyr Asn Ser His Asn Val Tyr Ile Met Ala Asp Lys Gln Lys Asn
        145                     150                 155                160
        Gly Ile Lys Val Asn Phe Lys Ile Arg His Asn Ile Glu Asp Gly Ser
                        165                 170                175
        Val Gln Leu Ala Asp His Tyr Gln Gln Asn Thr Pro Ile Gly Asp Gly
                        180                 185                190
        Pro Val Leu Leu Pro Asp Asn His Tyr Leu Ser Thr Gln Ser Ala Leu
                        195                 200                205
        Ser Lys Asp Pro Asn Glu Lys Arg Asp His Met Val Leu Leu Glu Phe
        210                     215                 220
        Val Thr Ala Ala Gly Ile Thr Leu Gly Met Asp Glu Leu Tyr Lys
        225                     230                 235

<210> SEQ ID NO 6
<211> LENGTH: 239
<212> TYPE: PRT
<213> ORGANISM: Artificial Sequence
<220> FEATURE:
<223> OTHER INFORMATION: Mutation of GFP, K4A

<400> SEQUENCE: 6

Met Val Ser Ala Gly Glu Glu Leu Phe Thr Gly Val Val Pro Ile Leu
1               5                  10                 15
Val Glu Leu Asp Gly Asp Val Asn Gly His Lys Phe Ser Val Ser Gly
                20                  25                 30
Glu Gly Glu Gly Asp Ala Thr Tyr Gly Lys Leu Thr Leu Lys Phe Ile
                35                  40                 45
Cys Thr Thr Gly Lys Leu Pro Val Pro Trp Pro Thr Leu Val Thr Thr
        50                      55                  60
Leu Thr Tyr Gly Val Gln Cys Phe Ser Arg Tyr Pro Asp His Met Lys
65                      70                  75                 80
Gln His Asp Phe Phe Lys Ser Ala Met Pro Glu Gly Tyr Val Gln Glu
                    85                  90                 95
Arg Thr Ile Phe Phe Lys Asp Asp Gly Asn Tyr Lys Thr Arg Ala Glu
                100                 105                110
Val Lys Phe Glu Gly Asp Thr Leu Val Asn Arg Ile Glu Leu Lys Gly
                115                 120                125
Ile Asp Phe Lys Glu Asp Gly Asn Ile Leu Gly His Lys Leu Glu Tyr
```

```
                130                 135                 140
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 7
<211> LENGTH: 239
<212> TYPE: PRT
<213> ORGANISM: Artificial Sequence
<220> FEATURE:
<223> OTHER INFORMATION: Mutation of GFP, G5A

<400> SEQUENCE: 7

Met Val Ser Lys Ala Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235
```

METHOD AND SYSTEM FOR MANIPULATING AND COMMUNICATING GENETIC CONSTRUCTS INDEPENDENT OF THEIR GENETIC SEQUENCE

CROSS REFERENCE TO RELATED APPLICATIONS

This application claims priority to U.S. Provisional Application No. 62/437,608, entitled "Method and System for Manipulating and Communicating Genetic Constructs Independent of their Genetic Sequence," filed Dec. 21, 2016, the entire contents of which is hereby incorporated by reference in its entirety for all purposes.

INCORPORATION BY REFERENCE OF ELECTRONICALLY SUBMITTED MATERIAL

Incorporated by reference in its entirety herein is a computer-readable amino acid sequence listing submitted herewith and identified as follows: 13,255 bytes ASCII (Text) file named "Sequence Listing SER16301," created Apr. 12, 2018.

ACKNOWLEDGMENT OF GOVERNMENT SUPPORT

This invention was made with government support under contract no. 1548676 awarded by the National Science Foundation. The government has certain rights in the invention.

FIELD

The disclosure relates to a genetic sequence security and manipulation system and to methods for securing communication of genetic sequences.

BACKGROUND

Genetic constructs such as proteins or plasmids may be components used not only in basic research, but also as both tools and products of research into biopharmaceuticals, biologics and biomaterials, potentially enhancing healthcare of people in addition to scientific knowledge. The easier, faster, and cheaper for researchers to test concepts, the more powerful the potential experimental results may be. By decoupling the manipulation and communication of genetic constructs from the DNA and amino acid sequences which underlie these genetic constructs, the subject disclosure enables researchers to more rapidly design and transmit actionable information about genetic objects faster, in a secured channel, and with greater functionality than would be possible if the sequence itself was the subject of manipulation and communication.

Current methods of manipulation and communication of genetic constructs depend heavily upon the sequence, whether DNA, amino acid or synthetic derivative, or other degenerative representations of those objects. When designing with these methods, sequences, as either representations of DNA or amino acids, are concatenated from 3' to the 5' for DNA, or from the N to C terminus for proteins. Manipulation by concatenation and substitution is frequently performed in a word processor, spreadsheet, or other kind of system such as an online web-app or custom specific-use script. After the initial sequence manipulation, further modification of the genetic construct requires adding or subtracting concatenated sequences, directly affecting the target sequence. If the designed construct is communicated to a 3rd party, whether for manufacture, analysis, or other reasons, it is sent as a document containing a single string of characters or list of strings of characters representing the underlying sequence.

Additionally, when more than one object is designed or communicated, a sequence for each construct may be required. These methods enable manipulation and communication of genetic constructs, but in a manner that is coupled and dependent upon their sequence. The coupling of sequence with manipulation and communication results in excessive complexity, lack of security, reduced functionality, and an increased chance of incorporating errors associated with textual manipulation (including frame-shifts, mutations, truncations, etc.) when compared with the utilizing a digital infrastructure capable of manipulation and communication of genetic constructs independent of their sequence.

The inventors have recognized the above problems relating to secure manipulation and communication of genetic constructs. Therefore, the inventors have developed a system and methods for securing manipulation and communication of sequences in order to at least partially address the above problems.

SUMMARY

The disclosure comprises a digital infrastructure paired with user input that can be accessed through a sequence computing device. This system may enable rapid manipulation and communication of genetic constructs, independent of the underlying genetic sequences of the genetic constructs, resulting in a system that is easier and faster to use, more secure, and has increased functionality. By separating the genetic sequence from the manipulation and communication process, the subject disclosure enables the user to design and communicate their genetic construct, also referred to herein as a target sequence, without having to engage with the inherent complexity in directly using strings of genetic sequences that can be several thousand characters long.

Enhancing the simplicity of manipulating and communicating genetic objects reduces the barrier to entry for manipulating genetic constructs by affording specialists in genetics the ability to more quickly accomplish simple tasks while also enabling non-specialists and specialists alike to now perform complicated tasks that would ordinarily be too technical.

Additionally, decoupling manipulation and communication of genetic constructs from the underlying genetic sequence of the genetic construct, also referred to herein as a source sequence, allows for enhanced security and privacy of valuable sequences while maintaining design productivity. Because the underlying genetic sequence of a genetic construct ultimately controls the structure and function of the genetic construct, the information regarding the DNA or an amino acid sequence itself may be highly valued. Securing the DNA or amino acid sequence from a competitor or another unauthorized entity is important to users whose sequences reveal trade secret or other proprietary information. Designing and communicating genetic constructs using an abstraction layer above the actual sequence itself secures the sequence while still enabling design, pricing, and communication of the genetic construct or information about the genetic construct.

Finally, manipulating genetic constructs by component rather than sequence enables increased functionality that was otherwise foreclosed when engaging with the sequence itself. For instance, decoupling the sequence from the genetic object enables the user to meaningfully trace variation as components are reused in other genetic objects without the need for computationally expensive string matching, maintain privileged segregation of data associated with specific components, manipulate constructs algorithmically, estimate useful and technical manufacturing, or functional properties, without requiring the exact underlying sequence, or calculate underlying sequence based on manufacturing concerns independent of a target sequence design.

DETAILED DESCRIPTION

Figure 1:
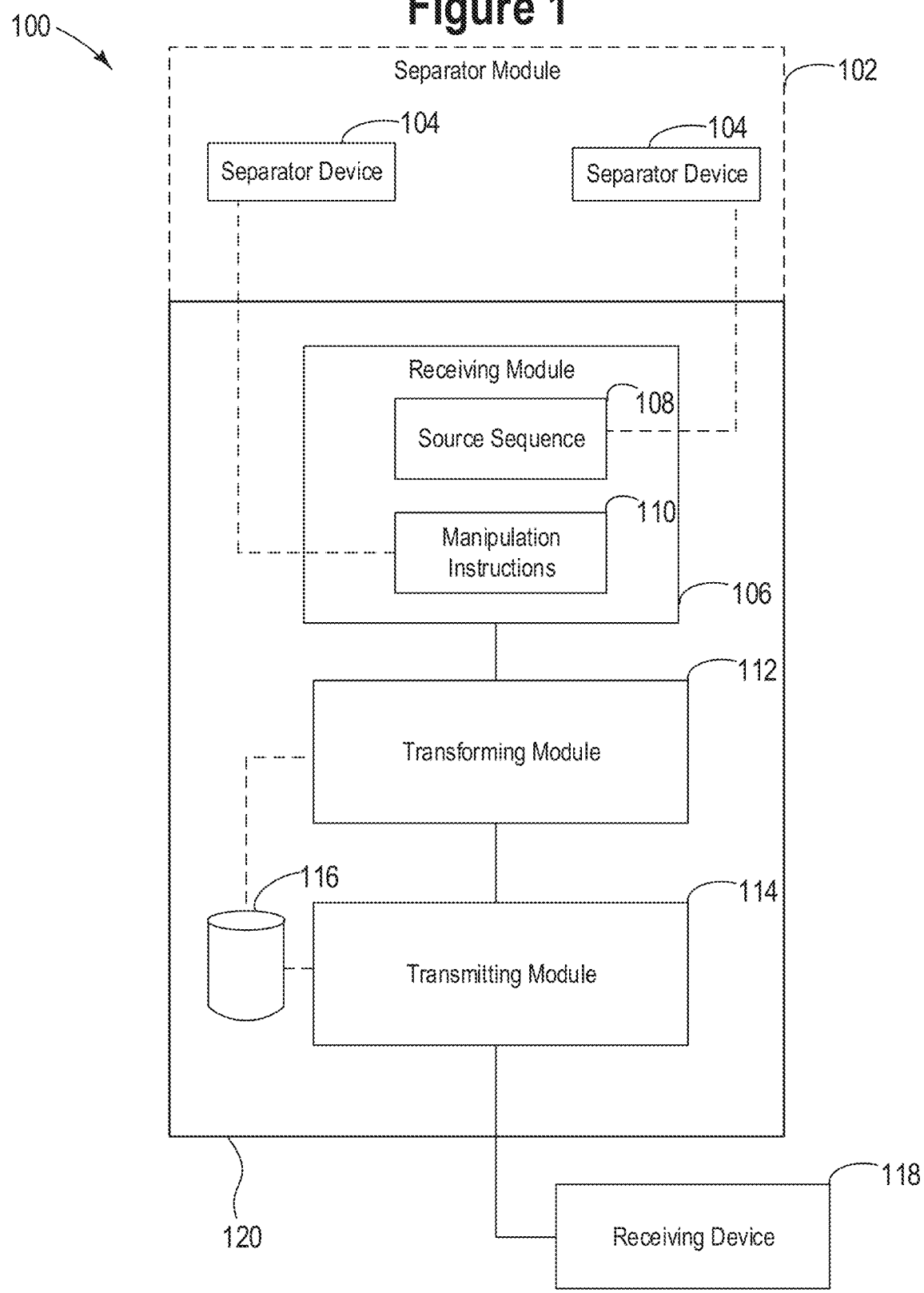
FIG. 1 shows a block diagram of an example sequence security system according to at least one embodiment of the disclosure.

Provided herein are a system and methods for maintaining a security of a genetic sequence during manipulation and communication of the genetic sequence between parties. As shown in FIG. 1, a sequence security system according to the present disclosure may include a security device in at least one example. The security device may enable the confidentiality of a target sequence to be maintained via separately receiving a source sequence and manipulation instructions. These received manipulation instructions may be applied to the received source sequence to transform the source sequence into a target sequence, in at least one example. Furthermore, the sequence security system may further include receiving devices that may receive the target sequence. For example, the security device of the sequence security system may transmit a target sequence to an authorized receiving device, following application of manipulation instructions to a source sequence.

By separately receiving the manipulation instructions and the source sequence, communication of the target sequence may be simplified, and a security of the target sequence may be increased. Moreover, by maintaining the source sequence and the manipulation instructions separate until they are received at the security device, improved computing efficiency may be realized. In particular, as each of the source sequence and the manipulation instructions are separately received at the security device, the security device may more efficiently identify the source sequence and the manipulation instructions, especially compared to previous approaches where both the manipulation instructions and the source sequence may have been transmitted together. Such improved efficiency may enable the security device to process information pertaining to forming a target sequence more quickly compared to previous approaches.

For example, rather than the security device having to determine which information refers to the source sequence and which information refers to the manipulation instructions within the same data transmission, the source sequence and the manipulation instructions are delivered separately. Thus, the security device does not have to separate the manipulation instructions and the source sequence. Rather, the manipulation instructions and the source sequence are received at the security device pre-separated.

Additionally, as the source sequence and the manipulation instructions are separately received at the security device, the information packet size required to send each of the source sequence and the manipulation instructions separately may be smaller compared to approaches where the manipulation instruction and the source sequence may have been sent in the same information packet. Thus, the approach developed by the inventors may have further advantages in regards to improving a processing efficiency, as relatively small information packets may need to be processed to determine each of the source sequence and the manipulation instructions rather than having to process large information packets that include both the source sequence and the manipulation instructions.

The sequence security system may be operated according to the methods as disclosed at FIG. 2 and FIGS. 8-10 to separately receive manipulation instructions and a source sequence, apply the manipulation instructions to the source sequence to transform the source sequence to a target sequence, and to transmit the target sequence. Furthermore, the system and methods for maintaining a security of a desired target sequence may further include example devices and methods for operating the sequence security system as described at FIGS. 3-10.

Turning to FIG. 1, FIG. 1 shows a block diagram of an example sequence security system 100 according to at least one embodiment of the disclosure. The example sequence security system 100 may comprise a plurality of devices. For example, the sequence security system 100 may include any one or combination of separator devices 104, a security device 120, and a receiving device 118. It is noted that any one or combination of these devices may be computing devices, also referred to herein as computing systems, that may perform one or more of the methods and processes described herein. It is to be understood that virtually any computer architecture may be used for a computing device without departing from the scope of this disclosure.

In different embodiments, these above mentioned devices may take the form of a mainframe computer, server computer, desktop computer, laptop computer, tablet computer, home entertainment computer, network computing device, mobile computing device, mobile communication device, gaming device, etc. Each of these devices may include a logic subsystem and a data-holding subsystem. Additionally, each of these devices may optionally include a display subsystem, communication subsystem, and/or other components. For example, these above discussed devices may also optionally include user input devices such as keyboards, mice, game controllers, cameras, microphones, and/or touch screens.

The logic subsystem of the devices may include one or more physical devices configured to execute one or more instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result. These instructions may be stored as modules on a data-holding subsystem of the computing devices.

The logic subsystem may include one or more processors that are configured to execute software instructions, such as the modules which are described herein. Additionally or alternatively, the logic subsystem may include one or more hardware or firmware logic machines configured to execute hardware or firmware instructions. Processors of the logic subsystem may be single core or multi-core, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

The data-holding subsystem may include one or more physical, non-transitory devices configured to hold data and/or instructions executable by the logic subsystem to implement the herein described methods and processes. For example, the modules described herein may be stored on the data-holding subsystem as instructions executable by the logic subsystem to implement the herein described methods and processes. When such methods and processes are implemented, the state of the data-holding subsystem may be transformed (for example, to hold different data).

The data-holding subsystem may include removable media and/or built-in devices. The data-holding subsystem may include optical memory (for example, CD, DVD, HD-DVD, Blu-Ray Disc, etc.), and/or magnetic memory devices (for example, hard disk drive, floppy disk drive, tape drive, MRAM, etc.), and the like. The data-holding subsystem may include devices with one or more of the following characteristics: volatile, nonvolatile, dynamic, static, read/write, read-only, random access, sequential access, location addressable, file addressable, and content addressable. In some embodiments, logic subsystem and the data-holding subsystem may be integrated into one or more common devices, such as an application specific integrated circuit or a system on a chip.

It is to be appreciated that the data-holding subsystem includes one or more physical, non-transitory devices. In contrast, in some embodiments aspects of the instructions described herein may be propagated in a transitory fashion by a pure signal (for example, an electromagnetic signal, an optical signal, etc.) that is not held by a physical device for at least a finite duration. Furthermore, data and/or other forms of information pertaining to the present disclosure may be propagated by a pure signal.

When included, a display subsystem may be used to present a visual representation of data held by the data-holding subsystem. As the herein described methods and processes change the data held by the data-holding subsystem, and thus transform the state of the data-holding subsystem, the state of the display subsystem may likewise be transformed to visually represent changes in the underlying data. The display subsystem may include one or more display devices utilizing virtually any type of technology. Such display devices may be combined with logic subsystem and/or the data-holding subsystem in a shared enclosure, or such display devices may be peripheral display devices.

Further, each of the devices may include a communication subsystem configured to communicatively couple the devices with one or more other computing devices. For example, sequence information may be transmitted between devices via the communication subsystem. The communication subsystem may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, communication subsystem may allow a computing system (i.e. computing device) to send and/or receive messages to and/or from other devices via a network such as the public Internet.

Turning now to the example sequence security system 100, the example sequence security system 100 may include a security device 120. Security device 120 may be a computing device including a plurality of modules for maintaining the confidentiality of a target sequence, in particular, a target genetic sequence. For example, security device 120 may include a receiving module 106, a transforming module 112, and a transmitting module 114. The receiving module 106 of security device 120 may receive information such as a source sequence 108 (i.e., a source genetic sequence) and manipulation instructions 110, and the receiving module 106 may receive the source sequence 108 and the manipulation instructions 110 separately. Furthermore, the example sequence security system 100 may include a database 116. Database 116 may include information about sequences identified by a unique id (e.g., Construct Object IDs, New Sequence IDs, etc.). The information about the sequences may include data such as the length, a hash of the sequence, the name, a description, functions, references, submission details, and construction limitations. In at least one example, database 116 may be configured to contain multiple tables with information to support the manipulation, storage and identification of the sequence, including but not limited to user data, properties, references, and construction rules. The manipulation data may also be identified in the database 116 by a unique ID (e.g., Manipulation Object ID).

The sequence data itself may be segregated from these other tables while being tied by a common identification key in order to permit access to various aspects of the data using a common identification number. The IDs for the sequences and manipulation data stored in database 116 may be assigned by the separator device, in at least one example. However, in other examples, the IDs for the sequences and manipulation data stored in database 116 may be assigned by receiving module 106.

The source sequence 108 may include any one or combination of a complete genetic sequence, a portion of a genetic sequence, a single complete genetic sequence, a portion of a single genetic sequence, a plurality of genetic sequences, and a plurality of genetic sequence portions. Additionally or alternatively, the source sequence may be assigned a unique ID. The manipulation instructions 110 may be instructions that may be applied the source sequence(s) 108. In some examples, the manipulation instructions 110 may include instructions for constructing a target genetic sequence by applying the manipulation instructions 110 to a source sequence(s) 108. The manipulation instructions 110 may include any one or combination of biological instructions that may be applied to the source sequence. For example, the manipulation instructions may include one or more of linear, combinatorial sequence, patch, and concatenated instructions to be applied to a source sequence(s) 108 in order to arrive at a target sequence. Other common manipulations of construct sequences may include but are not limited to, the combinatorial production of protein sets, mutation sets, mutation pools, scaffolded antibody design, protein tagging, combinatorial promoter sets, scaffolded receptor design, scaffolded enzyme design, multi-protein pools, multi-plasmid pools, gene cassette assembly and combination as well as genome assembly. However, the manipulation instructions 110 may be any one or combination of biological instructions which may be applied to the source sequence(s) 108 in order to transform the source sequence(s) to a target sequence. Additionally or alternatively the manipulation instructions may be assigned an ID. For example, the manipulation instructions may be assigned an ID that corresponds with the ID assigned to the source sequence to which the manipulation instructions are to be applied.

In at least one embodiment, the receiving module 106 may receive a source sequence 108 and manipulation instructions 110 from a separator module 102, where the separator module 102 may comprise a plurality of separator devices 104. The separator devices 104 of the sequence security system 100 may be computing devices storing either a source sequence (i.e., source genetic sequence) or manipulation instructions to be communicated to a receiving module 106 of the sequence security system 100.

In at least one example the separator devices may be computing devices including a sequence processor. The sequence processor may include instructions for communicating one or more of a source sequence and manipulation instructions. For example, the separator devices 104 may be computing devices including a sequence processor for communicating one or more of a source sequence and manipulation instructions to a receiving module such as receiving module 106. It is noted that while a separator device 104 may communicate both a source sequence and manipulation instructions, and a source sequence and manipulation instructions that may be indicated to both be portions of a single target sequence may not both be communicated by a separator device. Such separation of the source sequences and manipulation instructions that are identified as both necessary to arrive at a target sequence may protect the confidentiality of the target sequence. The separator devices 104 may communicate (i.e., transmit) one or more of a source sequence and manipulation instructions wirelessly in one example. However, in other examples, the separator devices 104 may communicate one or more of a source sequence and manipulation instructions via hardwire connection. In at least one example, the separator devices 104 may encrypt one or more of a source sequence 108 and manipulation instructions 110 prior to transmission to a receiving module.

The separator devices 104 may include only one of a source sequence and manipulation instructions in order to ensure confidentiality of a target sequence. Specifically, by only having one of a source sequence and manipulation instructions on an individual separator device 104, a target sequence, also referred to as a genetic construct, may not be discernable via a single separator device 104. Put another way, separating a source sequence 108 and manipulation instructions 110 by only allowing either a source sequence or manipulation instructions on each separator device 104, may maintain the confidentiality of a target sequence that may result from applying such manipulation instructions to the source sequence. Maintaining the confidentiality of a target sequence may be advantageous for protecting a proprietary target sequence in some examples. For example, via separating the source sequence 108 from the manipulation instructions 110, the example sequence security system 100 may prevent unauthorized users from accessing a target sequence, thus increasing the security of such information.

Therefore, in order to maintain confidentiality, receiving module 106 may receive the source sequence 108 from a first separator device 104, and the receiving module 106 may receive the manipulation instructions 110 from a second separator device 104 of separator module 102.

Figure 2:
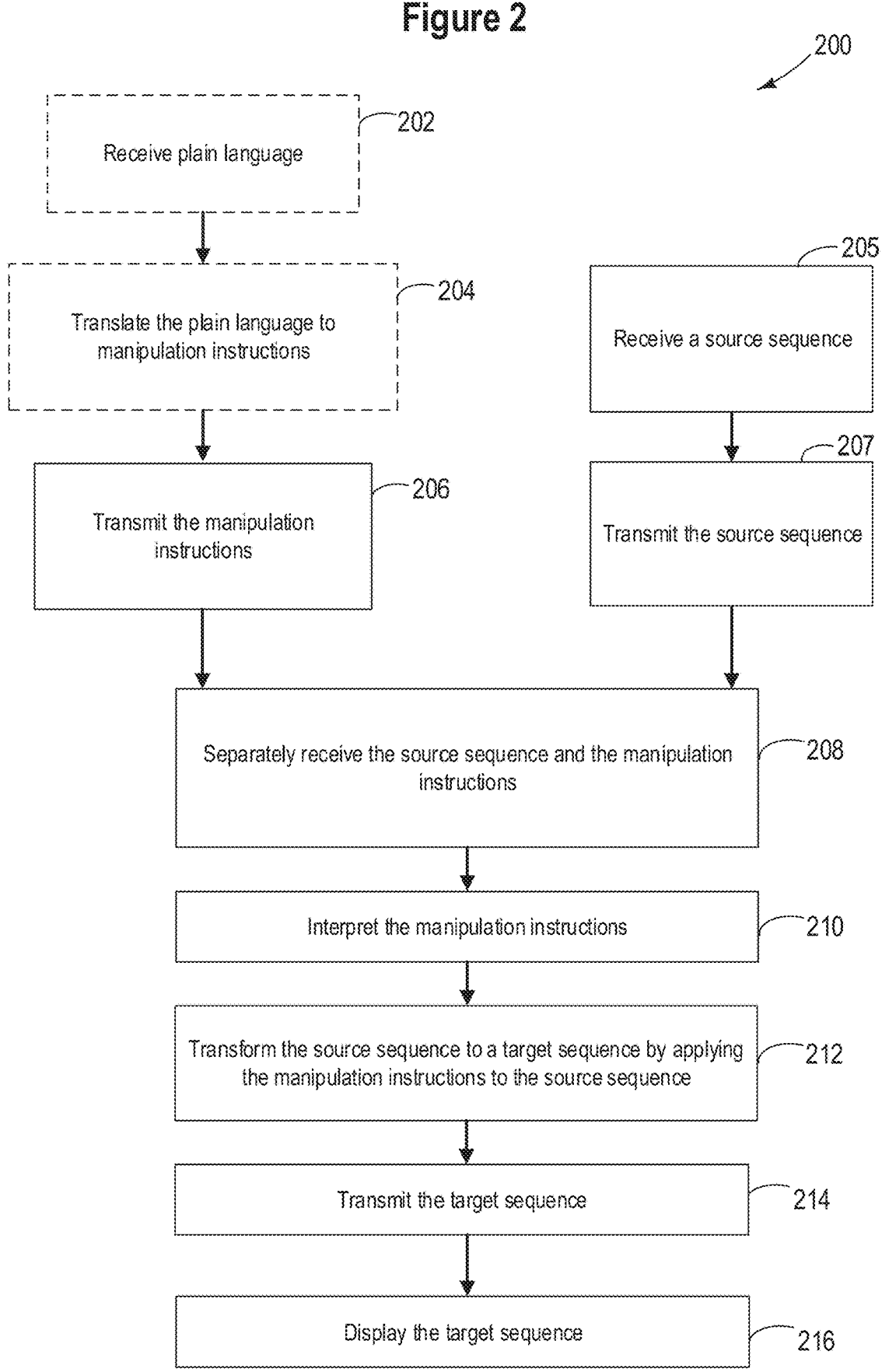
FIG. 2 shows a flow chart of an example method according to at least one embodiment of the disclosure.

In some examples, a separator device 104 that communicates manipulation instructions 110 to the receiving module 106 of the sequence security system 100 may first receive plain language and automatically translate the plain language to such manipulation instructions 110 prior to communicating the manipulation instructions 110 to the receiving module 106, as is described in more detail at FIG. 2. However, in other examples, the separator device 104 that communicates manipulation instructions 110 to the receiving module 106 may not have to translate plain language to manipulation instructions prior to communicating the manipulation instructions 110 to the receiving module 106. In some embodiments, a database 116 may be accessed in order to translate plain language to manipulation instructions 110.

In at least one example, separator module 102 may be physically integrated with security device 120. Additionally or alternatively, however, separator module 102 may be communicatively linked with the security device and not integrated with the security device 120. For example, a portion of separator devices 104 of the separator module 102 may be communicatively linked to the security device 120 without being physically integrated with the security device 120, and another portion of the security devices 104 may be physically integrated with the security device 120. In another example, all of the separator devices 104 of the separator module 102 may only be communicatively linked to the security device 120 without being physically integrated with the security device 120. The separator modules 104 may be communicatively linked to the security device 120 via a network. For example, the separator devices 104 may be communicatively linked to the security device 120 via a wireless connection. Additionally or alternatively, the separator devices 104 may be communicatively linked to the security device 120 via a hard wire connection.

Following receiving a source sequence 108 and manipulation instructions 110, the receiving module 106 may communicate with a transforming module 112 of the security device 120. The transforming module 112 may apply the manipulation instructions 110 to the source sequence 108. In some examples, the transforming module 112 may access a database 116 in order to determine the how to apply the manipulation instructions 110 to the source sequence 108. For example, the manipulation instructions 110 may provide a command to apply a set of biological instructions to a source sequence, and the transforming module 112 may then access a database 116 in order to determine the specific operations to carry out the manipulation instructions 110.

After the transforming module 112 has applied the manipulation instructions 110 to the source sequence 108, a target sequence may be determined. In at least one embodiment, the target sequence obtained via the transforming module 112 may be transmitted to a receiving device 118 via the transmitting module 114. In one embodiment, the transmitting module 114 may transmit the target sequence to a plurality of receiving devices 118. Additionally or alternatively, the target sequence may be displayed via the security device 100. For example, after verifying that a user has permission to view the target sequence, the security device 100 may display the target sequence via the security device (e.g. via a display of the security device 100).

In some embodiments, the target sequence transmitted to the receiving device 118 may be encrypted in order to further protect the confidentiality of the target sequence obtained via the transforming module 112. However, in other examples the target sequence may not be encrypted prior to transmission to a receiving device 118. The receiving device 118 may be a computing device configured to receive a transmitted target sequence. In some examples, the receiving device 118 may only be a device that is pre-authorized for transmission from the transmitting module 114. For example, sequence security system 100 may include a registry of authorized user to whom a target sequence may be transmitted. Additionally, a target sequence may be specified for a particular receiving device 118 or plurality of receiving devices 118 in order to increase the security of the target sequence. The transmitting module 114 may transmit the target sequence to the receiving device 118 via a wireless communication link to the receiving device 118 in some examples. The receiving device 118 may be wirelessly connected to the security device 120 via a network in some examples. Additionally or alternatively, the transmitting module 114 may transmit the target sequence to the receiving device 118 via a hard wire connection. Following transmission of the target sequence to the receiving device 118, the receiving device 118 may display the target sequence via a display of the receiving device 118.

Thus, described in FIG. 1 is an example sequence security system 100. The sequence security system 100 may include a separator module 102 communicatively coupled to a security device 120, and a receiving device 118 communicatively coupled to the security device. The security device 120 may comprise a plurality of modules including any one or combination of a receiving module 106, a transforming module 112, and a transmitting module 114. In some examples, the separator module may be physically integrated with the security device 120. Additionally or alternatively, the separator module may be communicatively coupled to the security device without being physically integrated with the security device. The separator module 102 may comprise a plurality of separator devices 104, and each of the separator devices 104 may either exclusively store a source sequence 108 or exclusively store manipulation instructions 110, and the separator devices 104 of the separator module 102 may separately communicate a source sequence and manipulation instructions to a receiving module of the security device 120. However, in some examples, a single separator device 104 may store a portion of a combination of a source sequence and manipulation instructions without storing all of the source sequence and the manipulation instructions to achieve the target sequence.

A transforming module 112 of the security device 120 may apply the manipulation instructions 110 to the source sequence 108 to obtain a target sequence, and the transmitting module 114 of the security device 120 may then transmit the target sequence obtained via the transforming module 112 to a receiving device 118 of the sequence security system 100. The receiving device 118 may then display the target sequence after receiving the target sequence from transmitting module 114 of the security device. In at least one embodiment, the target sequence may only be sent to receiving device 118 after verifying that receiving device 118 has a permission level that allows viewing of the target sequence. Additionally or alternatively, the target sequence may be protected via a password, biological lock, etc., and the target sequence may not be displayed until it has been verified that a user has permission to view the target sequence. Thus, a confidentiality of a target sequence may be better controlled.

Turning now to FIG. 2, FIG. 2 shows a flow chart of an example method 200 according to an embodiment the present disclosure. In some embodiments, method 200 may be carried out via a sequence security system as described above. For example, method 200 may be carried out by a security device of a security system, where the security device includes non-transitory computer readable instructions for performing the steps as described below in example method 200.

Method 200 may begin at step 202 by receiving plain language. The plain language received at step 202 may be instructions that include manipulation instructions in a form that is not usable for transforming a source sequence. In particular, the plain language may include instructions that are not usable for transforming a source sequence, as the plain language may be in a form that a processor of the security device is unable to execute. In at least one example, the plain language received at step 202 may include instructions that include technical terms indicative of manipulation instructions but which are not in a usable form for application to a source sequence.

The plain language may be received via a user input. The user input may be received via any one or combination of a voice command, physical input to a user interface (e.g., physical input to a touch screen, keyboard, mouse of a computing device, etc.), and optical recognition. In examples where step 202 of method 200 includes receiving plain language via a user input through a voice command, receiving the plain language may include sensing auditory information and determining whether the sensed auditory information includes plain language. The auditory information may be sensed via a microphone for example. If it is determined that the auditory information includes plain language, the plain language may utilized at step 204, as described in more detail below.

In examples where step 202 of method 200 includes receiving plain language via a user input through optical recognition, receiving the plain language may include optically sensing an object (e.g., paper with written instructions, an uploaded photograph, etc.) and determining if there is plain language present. If it is determined that the auditory information includes plain language, the plain language may be utilized at step 204. Machine learning algorithms may be applied to extract plain language from a user-generated scene, design, or physical construction.

Following receiving plain language at step 202, method 200 includes translating the plain language to manipulation instructions at step 204, where the manipulation instructions are instructions that are executable via the processor of the security device. In some examples, step 204 may include accessing a database, such as database 116, in order to translate the plain language to manipulation instructions. Translating the plain language received at step 202 to manipulation instructions may reformat the commands embedded in the plain language received at step 202 to manipulation instructions that are usable by the sequence security system. Put another way, though the plain language received at step 202 may include instructions for transforming a sequence, the plain language may be in an unusable form for application via the sequence security system (e.g., the processors of the security device, separator devices, receiving device). Thus, translating the plain language to manipulation instructions at step 204 may enable biological instructions received at step 202 in plain language to be translated into usable form manipulation instructions for the sequence security system devices. The ability to convert received plain language to manipulation instructions may be advantageous for several reasons. As one example, the ability to receive plain language and utilize the plain language to produce manipulation instructions may create a more user friendly process for manipulating source sequences. Furthermore, the ability to receive plain language to determine manipulation instructions may increase an efficiency for transforming a source sequence, as issues such as syntax errors may be reduced while also permitting suggestions and options to be presented.

Following translating the plain language to manipulation instructions at step 204, method 200 may include transmitting the manipulation instructions. In some examples, transmitting the manipulation instructions may include transmitting manipulation instructions to a receiving module of a security device. For example, the manipulation instructions may be transmitted to a receiving module of a security device as described in relation to FIG. 1.

Though method 200 may be described as receiving plain language at step 202, it may be appreciated that plain language may not be received and that manipulation instructions may instead be received. In such examples where manipulation instructions that are in a usable format for a sequence security device as opposed to plain language, method 200 may not include steps 202, 204, and 206. Instead, method 200 may include receiving manipulation instructions in a usable form via a user input, and the manipulation instructions may be transmitted, for example, to a receiving module of a security device. The method may then continue at step 208 in examples where manipulation instructions as opposed to plain language is received. Manipulation instructions may be received in any one or combination of the manners described above in relation to receiving plain language. However, instead of needing to translate the manipulation instructions following receipt of the manipulation instructions, these manipulation instructions may instead be transmitted and received at step 208 without a translation step.

At step 208, either following receiving plain language or receiving manipulation instructions, method 200 may include separately receiving a source sequence and manipulation instructions. For example, a receiving module of the sequence security system described in relation to FIG. 1 may separately receive a source sequence and manipulation instructions. In at least one example, the source sequence may originally be received via a user input at step 205 of method 200, prior to separately receiving the source sequence and the manipulation instructions at step 208. For example, at step 205, the source sequence may be received via any one or combination of manners for receiving a user input described above. The source sequence may be received at a security device, in at least one example, such as a separator module of a security device. Following receiving the source sequence at step 205, the source sequence may be transmitted to a receiving module of the security device at step 207. It is noted tha the source sequence that is transmitted is maintained separated from the manipulation instructions during transmission for security purposes. Maintaining the manipulation instructions and the source sequence instructions separate from one another during transmission to a receiving module of a security device may beneficially improve security of a target sequence, where the target sequence is a sequence resulting from applying manipulation instructions to the source sequence. Moreover, the separate transmission of the source sequence and the manipulation instructions may allow multiple entities with differing permission statuses to collaborate while still securing the target sequence.

Turning back to step 208, step 208 may include receiving a source genetic sequence without manipulation instructions in a first information packet and separately receiving manipulation instructions without the source genetic sequence in a second information packet. In at least one example, the source sequence and the manipulation instructions packets may be received at a receiving module of a security device. It is noted herein that reference to transmission of information refers to electronic transmission of information. For example, transmission of manipulation instructions, source sequences, and the first and second information packets may refer to electronic transmission of such information.

Until both the manipulation instructions and the source sequence have been received at step 208, the manipulation instructions and the source sequence have been kept separate from one another. Separately receiving a source sequence and manipulation instructions may increase a security of a target sequence (i.e., the resulting sequence following application of manipulation instructions to a source sequence).

Following separately receiving the source genetic sequence and the manipulation instructions at step 208, method 200 may include interpreting the manipulation instructions at step 210. Interpreting the manipulation instructions at step 210 may include accessing a database in some examples in order to determine which operations to apply to the source sequence based on the manipulation instructions. For example, the manipulation instructions may provide a command to apply a set of biological instructions to a source sequence, a database may be queried in order to determine the specific operations to apply to the source sequence in order to carry out the manipulation instructions. In some embodiments step 210 may be carried out via a transforming module of a security device, as described in reference to FIG. 1.

After interpreting the manipulation instructions at step 210, step 212 of method 200 may include transforming the source genetic sequence received at step 212 by applying the manipulation instructions. In some examples, applying the manipulation instructions at step 212 may include any one or combination of manipulation instructions as described in relation to FIG. 1.

Applying the manipulation instructions at step 212 of the method may transform the source sequence to a target sequence. Further, as the source sequence and the manipulation instructions for transforming the source genetic sequence were received separately, increased confidentiality regarding the target sequence, also referred to as the transformed sequence, may be achieved.

Following transforming the source sequence to obtain a target sequence by applying the manipulation instructions at step 212, method 200 may include transmitting the target sequence at step 214. For example, the target sequence may be transmitted to a receiving device. The target sequence may be transmitted via any one or combination of wireless communication and hardwire communication. Following step 214 of method 200, method 200 may include displaying the target sequence at step 216. For example, the target sequence received by the receiving device may be displayed via a display of the receiving device. In some examples, as detailed below, display of the target sequence may require successfully verifying that one or both of the receiving device and a user are permitted to have access to the target sequence. Following step 216, method 200 may exit.

Figure 3:
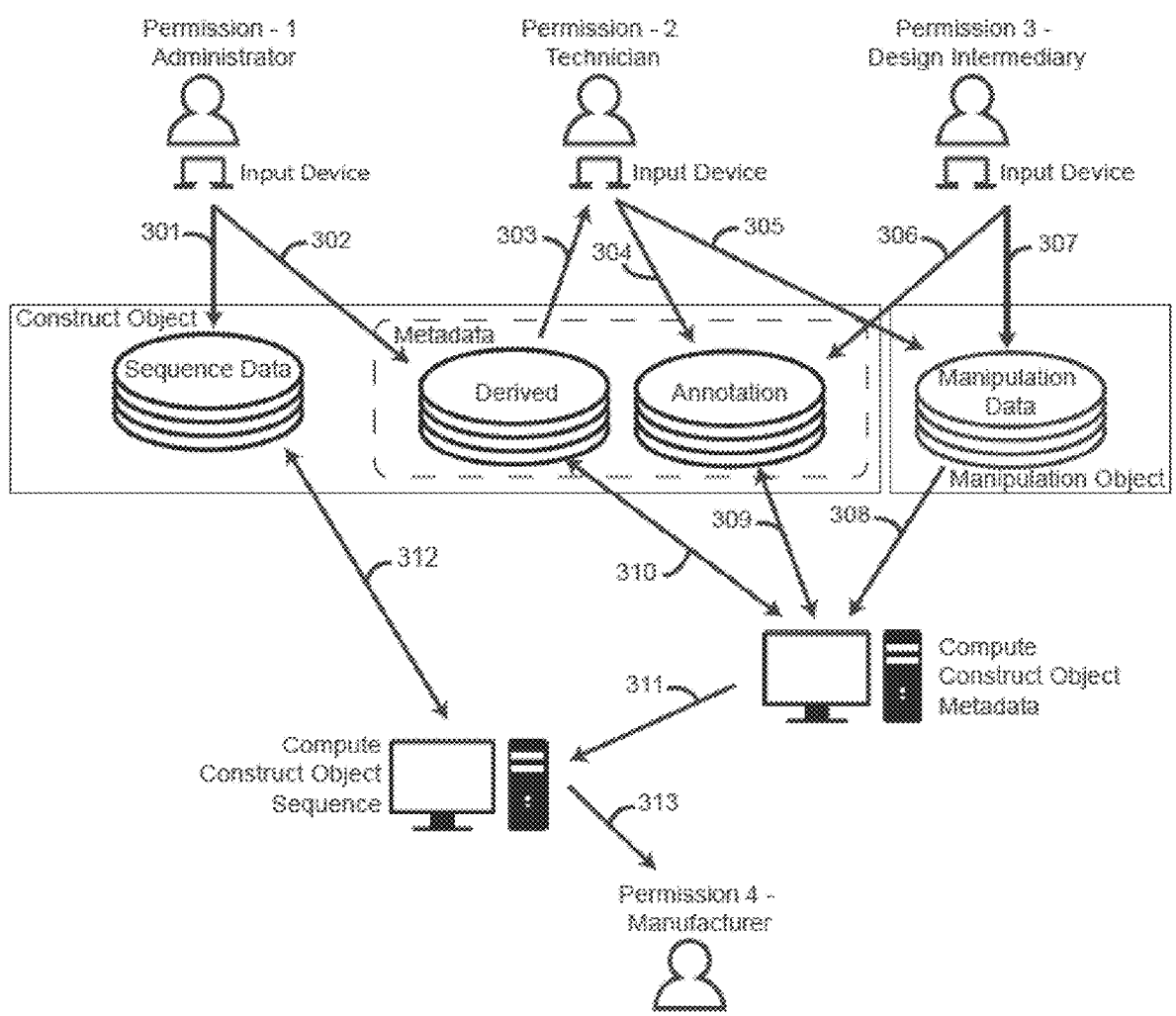
FIG. 3 shows a flow diagram of an example implementation and use-case of the disclosure.

Turning now to FIGS. 3 through 10, the steps described herein may be carried out by computing devices, and these computing devices may include the features described in relation to the computing devices of FIG. 1. Furthermore, it is noted that communication of data, such as sequence information, between the computing devices in FIGS. 3 through 10 may be carried out via communication subsystems of devices, such as the above described devices. For example, the communication subsystems of devices communicating data in FIGS. 3 through 10 may include any one or combination of the features discussed in relation to communication subsystems in FIG. 1 to communicate sequence information. Regarding FIG. 3, a flow diagram 300 of an example implementation and use-case of the disclosure is shown. As shown in FIG. 3, permission levels 1, 2, 3, and 4 may represent different levels of permissions for a user to engage with the disclosure. For example, permission level 1 may be an administrator permission level, permission level 2 may be a technician permission level, permission level 3 may be a design intermediary permission level, and permission level 4 may be a manufacturer permission level.

Permission level 1, permission level 2, and permission level 3 may only allow partial access to information regarding a target sequence. For example, permission level 1 may only allow access to a source sequence, permission level 2 may only allow access to metadata derived from the source sequence (while maintaining the confidentiality of the source sequence) as well as access to manipulation data, and permission level 3 may allow access to some metadata and manipulation data. In at least one example, the use-case shown at FIG. 3 may be carried out via a sequence security system, such as sequence security system 100 shown in FIG. 1.

At FIG. 3, Step 301 may include receiving a source sequence (e.g., a biological sequence) into data storage as a Construct Object with a unique ID. In some examples, the source sequence may be received via a user input. For example, the source sequence may be received via a user input at a first input device. Any one or combination of the user inputs described for receiving plain language may also be possible for receiving a source sequence. In one example, an administrator may input the source sequence.

Thus, in at least one example that may include a system such as sequence security system 100, the first input device receiving the source sequence 108 may be a first separator device, such as separator device 104. The first separator device may then transmit the source sequence 108 to a receiving module 106 of security device 120, and the receiving module 106 may transmit the source sequence 108 to a database, such as database 116.

The source sequence 108 may be stored at database 116 as a Construct Object with a unique ID. The unique ID of the Construct Object may also be referred to herein as a Construct Object ID. In at least one example, each source sequence may have an associated Construct Object ID.

After receiving the source sequence, Step 302 may include placing derived metadata from the source sequence (such as a source sequence length) into data storage, associated with a particular Construct Object ID. In one example, an administrator may use an input device to place the derived metadata into data storage.

In examples that may include system 100, for example, metadata derived from a source sequence 108 may be stored at database 116, where the metadata derived from the source sequence 108 is associated with the Construct Object ID. The metadata of the source sequence 108 may be derived directly from the source sequence 108 at Step 302. The metadata of the source sequence 108 may be derived at the separator device 104, in at least one example. However, in other examples, the metadata of the source sequence 108 may be derived via the security device 120. For example, the metadata of the source sequence 108 may be derived via receiving module 106 of the source sequence 108.

Continuing with the use-case example shown at FIG. 3, Step 303 may include receiving the metadata derived from the source sequence 108 that is associated with the Construct Object ID at a second separator device, where the second separator device is also referred to herein as a second input device. In one embodiment, the second separator device may be a separator device of a technician. Thus, the technician may access the metatadata derived from the source sequence 108 and that is associated with the Construct Object ID through the second input device, for example.

Step 304 of FIG. 3 may include receiving annotations as metadata. For example, a user (e.g., a technician) may enter annotations as metadata (other information about source sequence that cannot be derived from the sequence itself) through the second input device. Annotations may be associated with a particular Construct Object ID.

Put another way, at Step 304, the second separator device may receive annotations via a user input as metadata about the source sequence 108. The annotations received via the user input as metadata about the source sequence 108 may include information about source sequence 108 that cannot be derived from the sequence itself. These annotations received via the user input may be stored at database 116 and be associated with the Construct Object ID of the source sequence 108 in at least one example.

Turning now to Step 305 of FIG. 3, Step 305 may include creating a manipulation object with a unique ID and receiving manipulation mata (a first set of manipulation data) associated with the unique ID of the manipulation object. It is noted that the unique ID of the Manipulation Object may also be referred to herein as a Manipulation Object ID. In some examples, a technician may use an input device to create the manipulation object with the unique ID.

In examples where FIG. 3 is carried out via a sequence security system such as sequence security system 100, Step 305 may include receiving a user input (e.g., input from a technician) via the second separator device. Thus user input received via the second separator device at Step 305 may include manipulation data, such as instructions of manipulations to be applied to source sequence 108. The manipulation data may be assigned a Manipulation Object ID, and the Manipulation Object ID and the associated manipulation data may be received at security device 120 and stored in database 116. For example, the Manipulation Object ID and the associated manipulation data may be received via a receiving module 106 of security device 120, and the receiving module 106 may transmit the Manipulation Object ID and the associated manipulation instructions to database 116 for storage.

Moving to Step 306, Step 306 may include receiving additional annotations associated with the Construct Object ID. For example, a design intermediary may provide user input to a third input device (also referred to herein as a third separator device) to restrict, expand, suggest, decline, or otherwise enter additional annotations associated with the Construct Object ID. The annotations may be information that cannot be derived directly from the source sequence, for example.

In examples where FIG. 3 corresponds to a system such as sequence security system 100, the annotations associated with the Construct Object ID that are received via the third separator device may be transmitted to a receiving module of security device 120. Such annotations associated with the Construct Object ID may then be transmitted to database 116.

Moving now to Step 307, Step 307 may include receiving additional manipulation data (a second set of manipulation data), or modifying the manipulation data received at Step 305, associated with the Manipulation Object ID. As one example, a design intermediary may use a third separator device to enter the additional manipulation data, or to modify the manipulation data from Step 305.

In examples where the steps of FIG. 3 are carried out via a system such as sequence security system 100, the additional manipulation data of Step 307 that is received via user input at the third separator device may be transmitted to a receiving module 106 of security device 120. The additional manipulation data received at the receiving module 106 from the third separator device may then be transmitted for storage at database 116. It is noted that all manipulation data received at receiving module 106 of the security device 120 is maintained separate from the source sequence 108 and metadata associated with the source sequence within the receiving module for security purposes.

In examples where the additional manipulation data (the second set of manipulation data) modifies the manipulation data received at Step 305 (the first set of manipulation data), the additional manipulation data may override the manipulation data received at Step 305. Thus, at least some of the manipulation data received at Step 305 is not applied to the source sequence 108 in cases where additional manipulation data is received that modifies the manipulation data received at Step 305.

In at least one example, the additional manipulation data received via the third separator device may only be allowed to modify the manipulation data received at Step 305 after confirming a permission level. For example, prior to modifying the manipulation data received at Step 305 with the additional manipulation data, a permission verification step (e.g., a user log-in verification, etc.) may be performed to ensure that the modifications to the manipulation data received at Step 305 are allowed. In some examples, the permission verification step may be performed at the third separator device, and a notification of successful permission verification may then allow modification of the manipulation data received at Step 305 via additional manipulation data received via the third separator device.

Turning now to Step 308, Step 308 includes receiving manipulation object data for a particular Manipulation Object ID. For example, a processor, such as a security device, may receive the manipulation object data for a particular Manipulation Object ID. In examples where the security device may be security device 120, the manipulation object data for the particular Manipulation Object ID may be received at receiving module 106.

Turning now to Step 309, Step 309 may include receiving metadata associated with a particular Construct Object ID, creating a New Construct Object entry with a New Object ID, and entering the old annotation as a new annotation associated with New Construct Object ID.

Turning now to Step 310, Step 310 at FIG. 3 may include receiving derived metadata associated with the Construct Object ID and applying manipulation data from Manipulation Object ID. This results in New Derived Data that may be entered as associated with New Construct Object ID. In some examples a processor may carry out Step 310.

In examples where FIG. 3 is carried out via sequence security system 100, the security device 120 as described above may carry out step 310. In at least one embodiment, transforming module 112 of security device 120 may receive the Construct Object ID and the Manipulation Object ID described above. Then, the transforming module 112 may access database 116 to determine derived metadata associated with the Construct Object ID, and the transforming module 112 may access database 116 to determine manipulation data associated with the Manipulation Object ID.

After determining the derived metadata associated with the Construct Object ID and manipulation data associated with the Manipulation Object ID, transforming module 112 may apply the manipulation data to the derived metadata.

Turning now to Step 311 of FIG. 3, Step 311 may include receiving manipulation data associated with Manipulation Object ID. In some examples, the security device as described above may receive the Manipulation Data associated with the Manipulation Object ID. However, in other examples, a 2nd processor may receive the Manipulation Data associated with the Manipulation Object ID.

Following Step 311, Step 312 of FIG. 3 may include receiving source sequence data associated with Construct Object ID to which it applies the manipulation data from Step 311. The result of applying the manipulation data from Step 311 to the source sequence data associated with the Construct Object ID is a target sequence, also referred to herein as a new sequence. Data associated with the target sequence, may be entered into data storage, where it is associated with a New Construct Object ID. In some examples, the security device as described above may carry out Step 312. However, in other examples, a 2nd processor may carry out Step 312.

For example, in embodiments where sequence security system 100 is carrying out the steps shown in the example at FIG. 3, the transforming module 112 may receive the Construct Object ID and the Manipulation Object ID, and the transforming module 112 may then look up source sequence data associated with the Construct Object ID and manipulation data associated with the Manipulation Object ID at database 116.

After looking up the source sequence data associated with the Construct Object ID and manipulation data associated with the Manipulation Object ID, the transforming module 112 may then apply the manipulation data to the source sequence data to obtain a target sequence. The transforming module may then assign a New Construct Object ID to the target sequence, and the New Construct Object ID along with data associated with target sequence may be stored at database 116, for example.

Moving to Step 313 of FIG. 3, Step 313 may include transmitting the target sequence data associated with the New Construct Object ID to a receiving device-enabling manufacturing of the new sequence. In some examples, a manufacturer may receive the target sequence data associated the New Construct Object ID.

In examples where the steps of FIG. 3 are carried out via sequence security system 100, as Step 313 transmitting module 114 of security device 120 may access database 116 and retrieve the target sequence data associated with the New Construct Object ID. Then the transmitting module 114 may transmit the target sequence data associated with the New Construct ID to a receiving device 118.

In at least one example, the transmitting module 114 may first receive a request prior to accessing database 116 for the target sequence data associated with the New Construct Object ID and before transmitting the target sequence data. For example, in some cases security device 120 may receive a request to send target sequence data to receiving device 118 via a user input.

Prior to transforming module 114 retrieving and sending target sequence data, the transforming module 114 may first perform a permission verification step. Such a permission verification step may include checking a permission level of a user making a request to transmit target sequence data. Furthermore, in at least one example, the transmitting module may further verify that a receiving device 118 that is to receive the target sequence also has permission to receive the target sequence. These verification steps may require login information from users making transmitting requests and users that are to receive the target sequences. Additional security measures, such as encryption of the target sequence during transmission, password protecting the target sequence, etc. may be taken to ensure that access to the target sequence is controlled.

Thus, as shown in FIG. 3, permission levels 1, 2, 3, and 4 may represent different levels of permissions for a user to engage with the disclosure. The example implementation and use-case may include multiple separator devices 104, through which permission levels 1-3 may access security devices 120 via wireless or wired communicative link. Administrator deposits source sequence data through separator device 104 into security device 120. Design Intermediary accesses security device 120 via separator device 104 to provide meta-data about the source sequence. Technician uses separator device 104 to access meta-data and deposit manipulation instruction in security device 120, which applies manipulation instructions to source sequence to transform source sequence into target sequence. Finally, manufacturer receives target sequence from security device 120.

Figure 4:
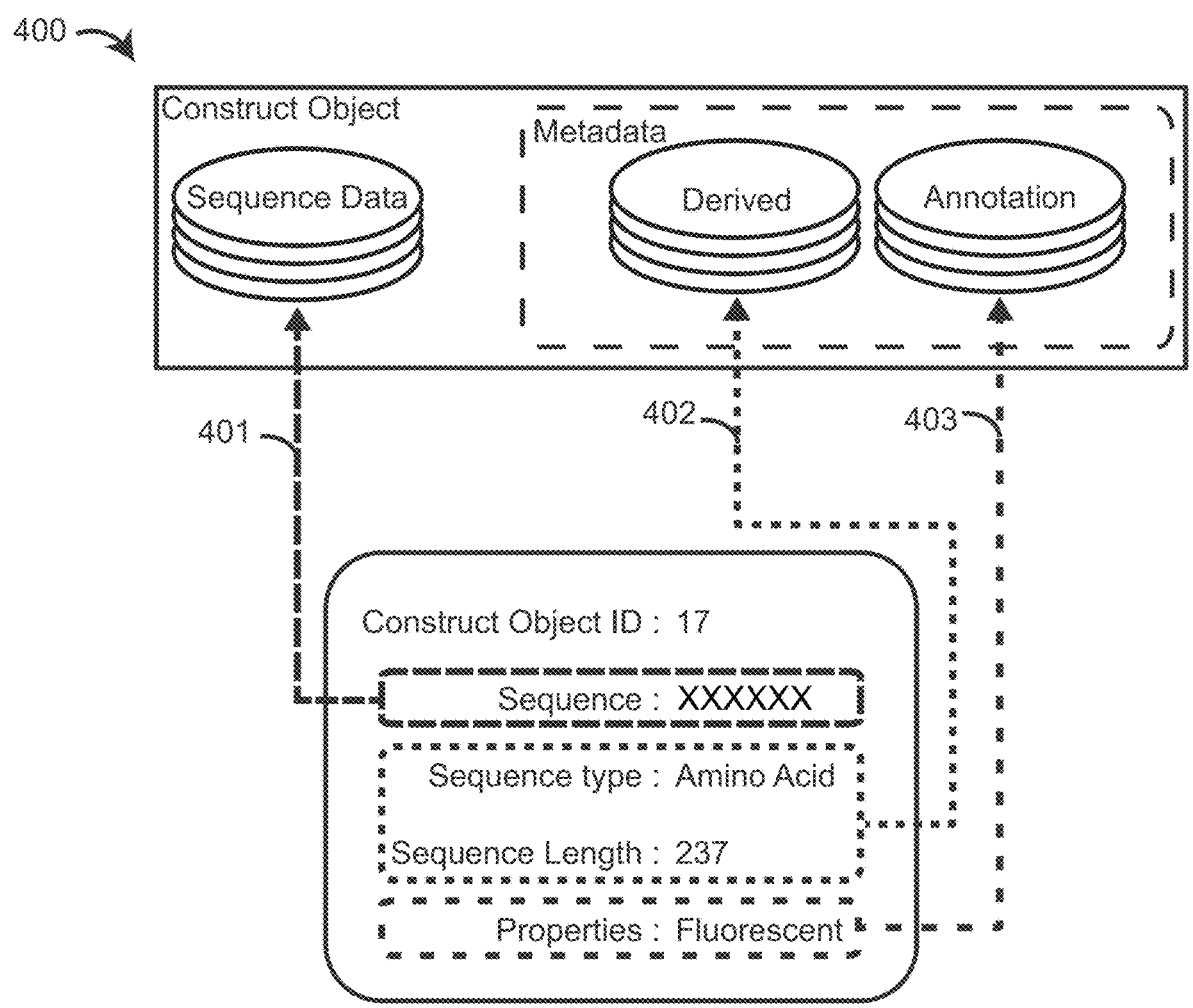
FIG. 4 shows a flow diagram of example entries that may be made to the Construct Object.

Turning now to FIG. 4, FIG. 4 shows a flow diagram example entries 400 that may be made to the Construct Object, also referred to herein as a source sequence, according to one embodiment of the present disclosure. Each Construct Object may possess a unique ID, also referred to herein as a Construct Object ID. Tied to this Construct Object ID may be two categories of data: sequence data and metadata. Metadata can be further divided into derived and annotation metadata, in at least one example. In at least one embodiment, the example at FIG. 4 may be employed via a sequence security system, such as sequence security system 100.

Turning first to Step 401 of FIG. 4, Step 401 may include entry of sequence data, where the sequence data may be an entry of the biological sequence, either amino acid or nucleic acid, or various other representations. For example, the sequence data may be received via a user input at a separator device 104. Additionally, the sequence data may be received at a receiving module 106 of security device 120. Such sequence data may further be received and stored at database 116.

Moving now to Step 402 of FIG. 4, Step 402 may include deriving data that may be deduced directly from the sequence itself, such as sequence length, hydrophobicity, etc. In at least one example, the sequence may be processed to obtain derived data at a separator device 104. However, in other examples, the sequence may be processed to obtain derived data at receiving module 106. The derived data of the sequence may be stored in database 116, where a unique ID (e.g., Construct Object ID,) may be associated with both the derived data and the sequence data.

In Step 403 of FIG. 4, annotation data associated with the sequence may be received, and not necessarily determined directly based on the sequence itself. Examples of the annotation data may include property/function, use-case, reference, etc. In some examples, the annotation data may be received via a user input (e.g., a user input received at separator device 104, a user input received at a receiving module 106, etc.). This annotation data associated with the source sequence may be stored at database 116 and also be associated with the unique ID (e.g., Construct Object ID) of the sequence.

Figure 5:
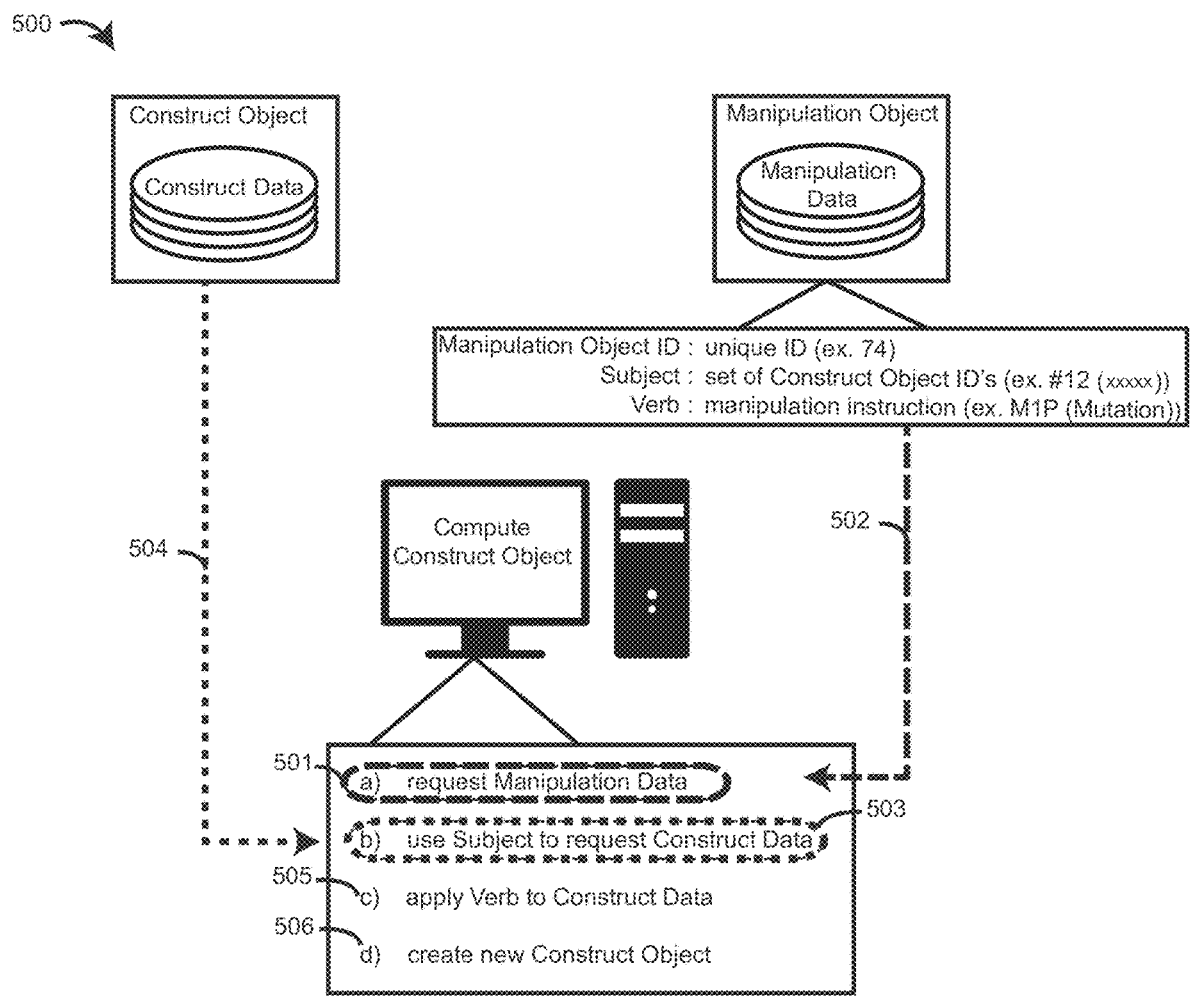
FIG. 5 shows an example flow diagram of details for storage of Manipulation Data and the computation/creation of a new Construct Object according to one embodiment of the present disclosure.

Turning now to FIG. 5, FIG. 5 shows a flow diagram 500 of example details for storage of Manipulation Data and the computation/creation of a target sequence, also referred to herein as a New Construct Object, according to one embodiment of the present disclosure. In at least one embodiment, the example at FIG. 5 may be part of the storage of a sequence security system 100, such as sequence security system 100 shown in FIG. 1.

In some examples, storage of manipulation data and the computation/creation of a target sequence may involve a processor, such as a processor of security device 120. The processor may compute a Construct Object, also referred to herein as a source sequence, and may access data storage devices for Construct Objects and Manipulation Objects (e.g., database 116). Manipulation data may include a subject, the Construct Object ID to which the manipulation will be applied, and a verb describing how the subject should be changed. Furthermore, the manipulation data is tied to a unique Manipulation Object identified by a unique ID, also referred to herein as the Manipulation Object ID. In at least one example, the manipulation data may be in plain language, as opposed to the manipulation data having to be written in computing language.

Thus, the subject, the Construct Object ID to which the manipulation will be applied, and the verb describing how the subject should be changed may be written as they would be spoken, instead of being written in a specific computing language. The plain language manipulation data may be translated at a separator module or at a receiving module of a sequence security system, in at least one example.

Turning to Step 501 of FIG. 5, Step 501 of FIG. 5 may include the processor performing a computation on the source sequence, also referred to herein as a construct object, requests manipulation data tied to a particular Manipulation Object ID, which is delivered at Step 502. That is, the Manipulation Object ID may be transmitted to the device of the processor responsive to the process requesting manipulation data tied to a particular Manipulation Object ID.

For example, in cases where FIG. 5 is applied to a sequence security system such as sequence security system 100, the transforming module 112 of security device 120 may receive a source sequence 108, and the transforming module 112 may request manipulation data tied to a particular Manipulation Object ID by querying database 116 for such manipulation data.

Turning to Step 503, Step 503 may include the processor performing a computation on the source sequence, also referred to herein as a construct object, requests construct data associated with the Construct Object ID from database 116, wherein the Construct Object ID is associated with the source sequence in database 116. In at least one example, the Construct Object ID may be contained in the requested manipulation object. The construct data may be delivered to the device of the processor at Step 504 responsive to the request for construct data generated by the processor. It is noted that the processor may be a processor of a security device, such as security device 120.

Moving to Step 505 of FIG. 5, Step 505 may include the processor performing computations on the construct object applying the Verb from manipulation data associated with the Manipulation Object ID to the construct data retrieved at Step 504.

As further shown at Step 506 of FIG. 5, Step 506 may include the processor performing the computation on the construct object creates a target sequence, where the target sequence is also referred to herein as a New Construct Object. The target sequence may be achieved via the processor performing the computation specified by the manipulation data on the construct data during the computation in Step 505. This target sequence, also referred to herein as the New Construct Object, will be identified with a new unique Construct Object ID.

Figure 6:
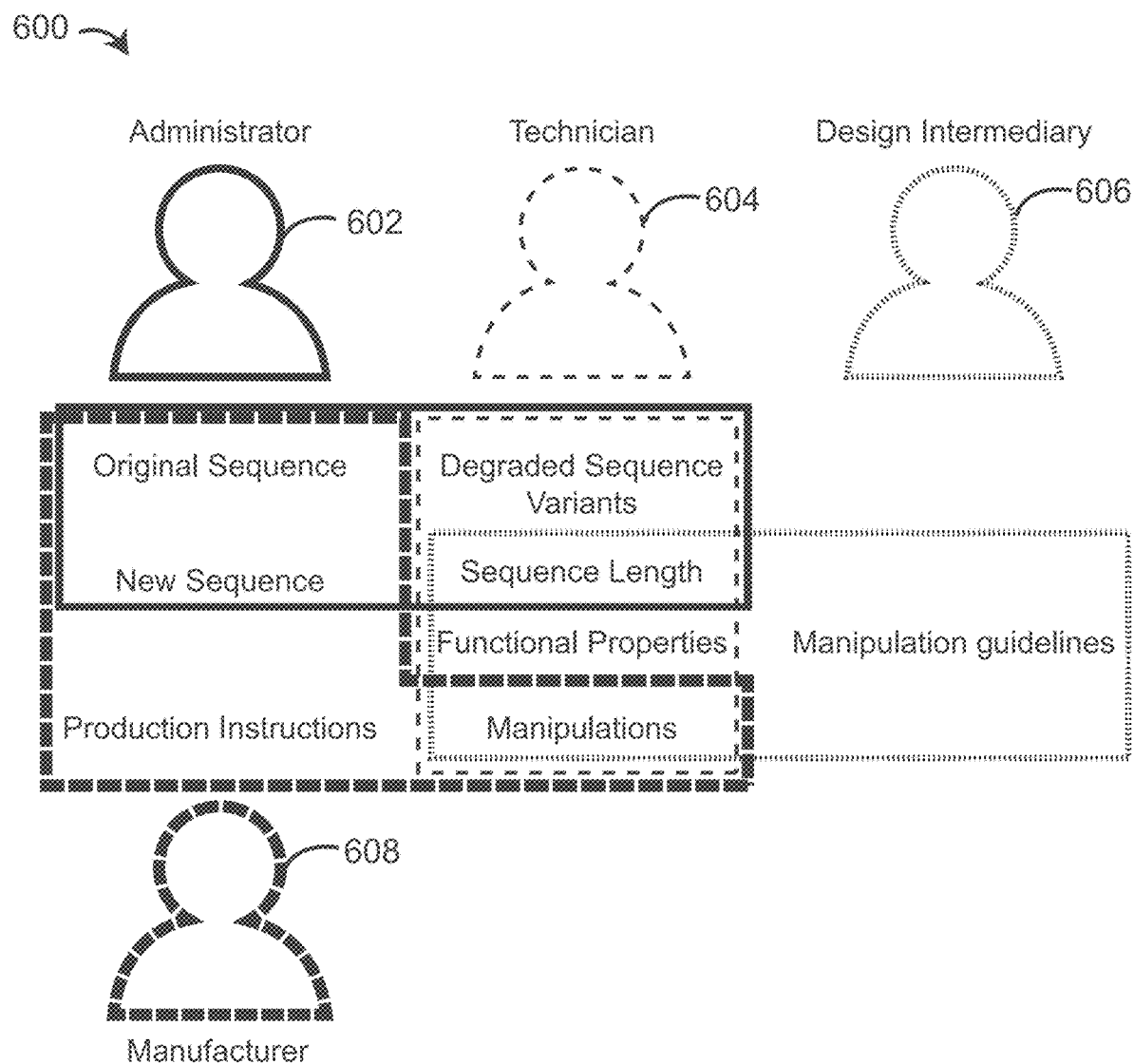
FIG. 6 shows example segregated permissions that may be provided in one embodiment of the present disclosure.

Turning now to FIG. 6, FIG. 6 shows a diagram 600 of example segregated permissions that may be provided in one embodiment of the present disclosure. As shown in FIG. 6, in an example, segregated permissions may be provided—resulting from separable data and functions. However specific access to any given data-set or function may be adjusted, depending on the specific permission-needs at hand. Differing privileges associated with variously permissioned user-types are outlined. In at least one example, the different permission-sets may be labeled administrator 602, technician 604, design intermediary 606, and manufacturer 608 permission sets. These permission-sets may be the same user entity, distinct entities, or distributed equally or unequally between a couple or several entities. Permission-sets may also be segregated virtually, through use of computer-based permissions, or physically, through distinct devices, or a combination thereof.

The example administrator permission-set 602 is indicated by a thin solid line. As shown at FIG. 6, the administrator permission-set 602 may include one more of access to a source sequence, degraded source sequence variants, a sequence length, and a target sequence (also referred to herein as a new sequence). However, the administrator permission-set 602 excludes access to production instructions, functional properties of the source sequence, manipulation instructions, and manipulation guidelines.

The example technician permission-set 604 is indicated by a thin dash line. As shown at FIG. 6, the technician permission-set 604 may allow access to one or more of degraded source sequence variants, sequence length, functional properties, and manipulation instructions. However, the technician permission-set 604 excludes access to the source sequence, a target sequence, production instructions, and manipulation guidelines.

The example design interiary permission-set 606 is indicated by a thin solid line. As shown at FIG. 6, the design intermediary permission-set 606 may allow access to one or more of the source sequence length, manipulation guidelines, functional properties of the source sequence, and the manipulation instructions. However, the design intermediary permission-set 606 prevents access to the source sequence, the target sequence, the production instructions, and degraded source sequence variants.

The example manufacturer permission-set 608 is indicated in thick dash. The manufacturer permission-set 608 may include access to one or more of the source sequence, manipulation instructions, the target sequence, and production instructions. The manufacturer permission-set 608 prevents access to the degraded sequence variants, the length of the source sequence, functional properties of the source sequence, and manipulation guidelines.

By segregating the information via various permission-sets such as shown in FIG. 6, a security of a target sequence may be maintained while still allowing users to perform their various roles to produce the target sequence.

In one embodiment, the disclosed system provides the ability to separate access to data and functions amongst several permission sets, affording productive collaboration towards the manipulation and communication of biological construct information without any single permissioned group having access to all information. In other words, each permissioned-user has access to only the data and functions necessary to carry out its role.

Figure 7:
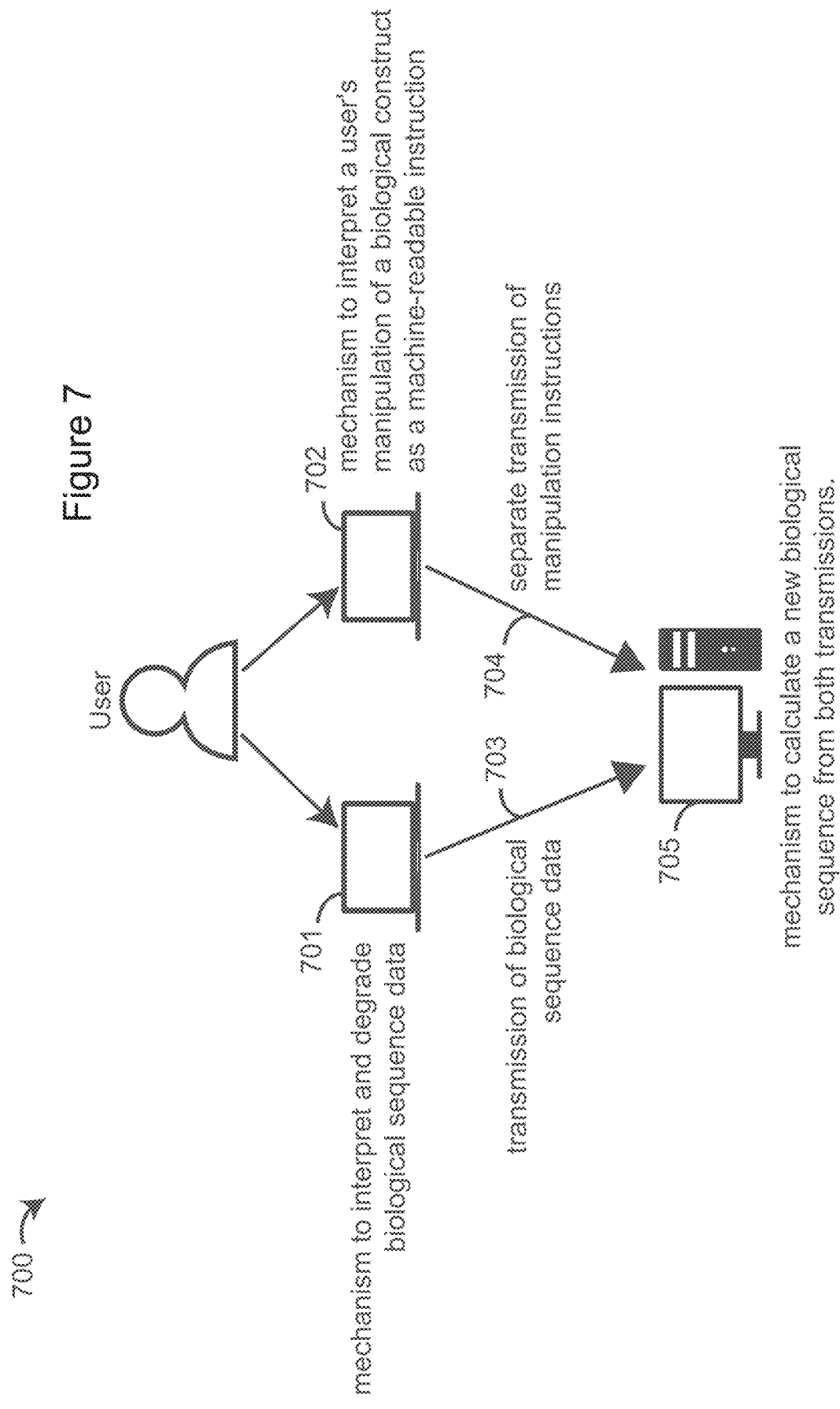
FIG. 7 shows additional example features of the disclosure according to one embodiment.

Moving now to FIG. 7, FIG. 7 shows a flow diagram 700 of additional example features of the disclosure according to at least one embodiment. In particular, FIG. 7 shows a series of steps according to an embodiment of the present disclosure. In at least one example, the steps shown at FIG. 7 may be carried out via a system such as sequence security system 100.

Turning first to Step 701, Step 701 may include a mechanism to interpret and degrade biological sequence data, where the biological sequence data is also referred to herein as a source sequence. Interpretation of the source sequence can be done through a device receiving a user input, where the user input includes source sequence data. In at least one example, the interpretation and degradation of the source sequence may be carried out via separator device 104. The mechanism to interpret and degrade the source sequence can also degrade the source sequence to a lesser specificity yet still be actionable for the purpose at hand. The level of obfuscation, ranging from none, to various kinds of partial, to complete obfuscation and only considering the length of the sequence, can be determined based on a user input.

Turning to Step 702 of FIG. 7, Step 702 may include interpreting an intended manipulation of the source sequence, for example a biological construct, as a machine-readable instruction. For example, the intended manipulation of the source sequence may be determined via a separator device 104. The source sequence may be received via a user input at the separator device, in at least one embodiment. Any one or combination of manners for receiving a user input described herein may possible for receiving the source sequence at Step 702.

Moving to Step 703, of FIG. 7, biological sequence data may be transmitted. For example, the biological sequence data may be transmitted to a receiving module of a security device.

At Step 704, a separate transmission of manipulation instructions to the same receiving module may be carried out. Thus, the manipulation instructions and the biological sequence data may be maintained separate from one another until the manipulation instructions and the biological sequence data have been received at the receiving module of the security device.

At Step 705, of FIG. 7, a mechanism calculates a new biological sequence, also referred to herein as a target sequence, derived from transmitted data in Step 703 & Step 704. That is, the manipulation transmitted at Step 704 may be applied to the biological sequence data transmitted at Step 703 to calculate the new biological sequence. In at least one example, the mechanism may be the security device of the receiving module, and the security device may carry out the calculation of the new biological sequence by applying the manipulation instructions to the biological sequence data.

Figure 8:
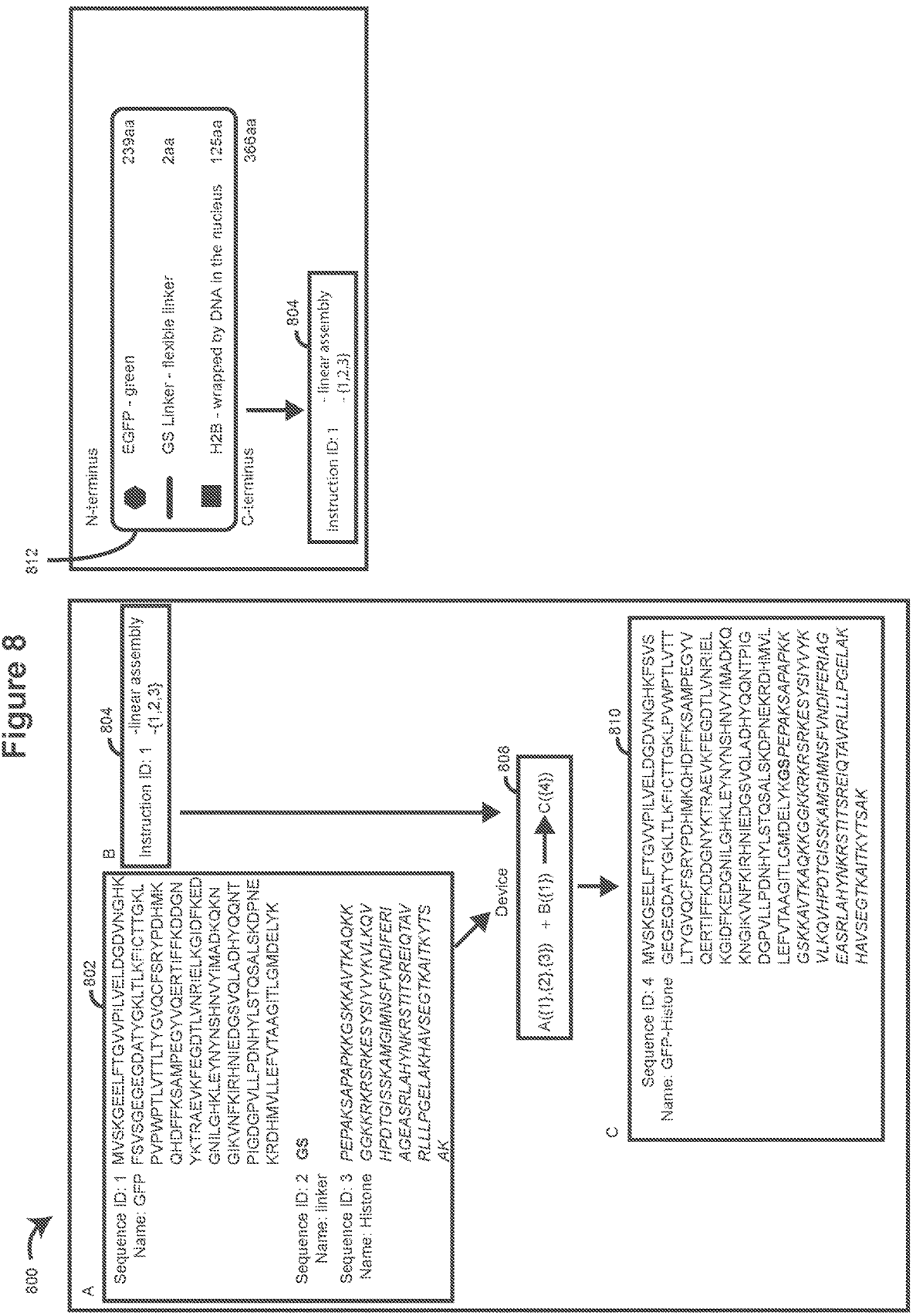
FIG. 8 shows a schematic flow diagram of a first example communication flow according to at least one example of the present disclosure, including SEQ. IDs 1-4.

FIG. 8 shows a schematic flow diagram of a first example communication flow 800 according an example of the present disclosure. Communication flow 800 may be a communication flow of a sequence security system in at least one example. In example communication flow 800, a source sequence 802 and manipulation instructions 804 may be separately received via a device 808. The source sequence 802 and the manipulation instructions 804 may be on separator devices. For example, the source sequence 802 and the manipulation instructions 804 may be each on different separator devices, such as the separator devices of the separator module described in relation to FIG. 1. Additionally or alternatively, the source sequence 802 and the manipulation instructions 804 may be physically integrated with device 808, where device 808 may be a security device as described in relation to FIG. 1. The source sequence 802 and the manipulation instructions 804 may include any one or combination of source sequences and manipulation instructions as described above in relation to FIGS. 1 and 2. For example, in communication flow 800, the source sequence 802 illustrated comprises a plurality of sequences.

In particular, the source sequence 802 comprises three sequences. Each of the sequences of source sequence 802 may be assigned a sequence ID. In the example illustrated at FIG. 8, of the source sequence 802, the first sequence has a sequence ID of "1" assigned to it, the second sequence has a sequence ID of "2" assigned to it, and the third sequence has a sequence ID of "3" assigned to it. Thus, each of the sequences of source sequence 802 is assigned a unique sequence ID. In addition to a sequence ID, the sequences of the source sequence 802 may be assigned names. In particular, in the example illustrated at FIG. 8 the first sequence is named GFP, the second sequence is named linker, and the third sequence is named histone. Other properties relevant to any step in the process may be similarly assigned.

Regarding the manipulation instructions 804, the manipulation instructions may also be assigned an instruction ID. For example, as illustrated in communication flow 800, the manipulation instructions 804 may be assigned an instruction ID "1". In other examples where there may be a plurality of instructions, each of the plurality of instructions may be assigned a unique instruction ID, similarly to the sequences of the source sequence. The plain language technical specifications 812 are processed to become the manipulation instructions 804, such as described at method 200, for example. That manipulation instructions are transmitted to the device 808, and the manipulation instructions are assigned an ID It will be appreciated that although numbers may be used to provide IDs for the sequences and the instructions, any unique identifier may be possible. For example, any one or combination of letters, numbers, graphic representations, and colors may be possible.

Once these unique sequence IDs and instruction IDs may be assigned to sequences of the source sequence 802 and the manipulation instructions 804, respectively, device 808 may utilize these unique sequence IDs and instruction IDs to ensure that the correct manipulation instructions are applied to the correct source sequence. For example, following receiving the source sequence 802 and the manipulation instructions 804 and their respective IDs, the device 808 may apply the received manipulation instructions 804 to the received source sequence 802 to transform the source sequence 802 to a target sequence 810, utilizing the sequence IDs and instruction IDs to match the manipulation instructions to the source sequence.

In the example illustrated at FIG. 8, the sequences of the source sequence may be linked in accordance with the linear assembly instructions provided by manipulation instructions 804 to link sequences of the source sequence 802. For example, the manipulation instructions 804 assigned an instruction ID of "1" may be applied to sequences associated with sequence IDs 1, 2, and 3, and the manipulation instructions 804 may link the sequences of the source sequence 802 in order of sequence IDs 1, 2, and then 3. Thus, the resulting target sequence 810 may be sequence 1, sequence 2, and sequence 3 linked together in that order. The target sequence 810 may then be assigned a unique sequence ID. In examples where there may be multiple target sequences 810, each of the target sequences 810 may be assigned a unique sequence ID. Assigning a unique sequence ID to each of the target sequences 810 may assist in development of another target sequence in some embodiments. For example, in some embodiments it may be desirable to further manipulate a target sequence 810. Thus, in such examples, one or a plurality of the target sequences 810 may be utilized as a source sequence 810, and there may be manipulation instructions 804 developed for application to the target sequences 810. In examples where a target sequence 810 may be utilized as a future source sequence 802, the sequence ID assigned to the target sequence 810 may be useful for ensuring that the sequences are being properly manipulated.

As source sequence 802 and manipulation instructions 804 are kept separate until they are received at device 808, the confidentiality of the target sequence 810 may be maintained prior to application of the manipulation instructions 804 to the source sequence 802 via device 808. Thus, access to the target sequence 810 may be controlled, the target sequence 810 may only be accessed via device 808, in some examples. Additionally or alternatively, the target sequence 810 may be transmitted to a receiving device, and the target sequence 810 may then be viewable via device 808 and the receiving device.

Figure 9:
FIG. 9 shows a schematic flow diagram of a second example communication flow according to at least one example of the present disclosure, including SEQ. ID 1 and SEQ IDs 5-7.

Turning now to FIG. 9, FIG. 9 shows a schematic flow diagram of a second example communication flow 900 according to an example of the present disclosure. Similarly to communication flow 800, communication flow 900 may be a communication flow of a sequence security system in at least one example. Communication flow 900 may share many similarities to the communication flow 800. Therefore, similar features are numbered similarly. The main difference between the communication flow described in relation to FIG. 8 and the communication flow 900 is the specific source sequence 802 and manipulation instructions 804 utilized. In particular, rather than a plurality of sequences being utilized as a source sequence 802 as in communication flow 800, a single sequence is the source sequence 802 in communication flow 900. The source sequence 802 in communication flow 900 may be a single sequence, as the manipulation instructions 804 that are applied to the source sequence 802 are mutation instructions as opposed to linking instructions. Put another way, the manipulation instructions 804 (which are assigned an instruction ID "2" in this example) may be mutation instructions to alter an amino acid at a certain position. For example, manipulation instructions 804 may include instructions to mutate an S at position 3 to an A. Additionally or alternatively other mutation instructions may be included. For example, mutation instructions to mutate a position 4 K to an A may additionally or alternatively be included. Further, the manipulation instructions 804 may additionally or alternatively include mutation instructions to mutate a position 5 G to an A.

Thus, in examples where the manipulation instructions 804 may be mutation instructions, only one sequence may be necessary for source sequence 802. It will be appreciated, however, that multiple sequences may also be possible for source sequence 802 in examples where manipulation instructions 804 include mutation instructions. In such examples, the mutation manipulation instructions 804 may be applied to each of the multiple sequences. Further still, in examples where the manipulation instructions 804 may include multiple biological instructions, these multiple biological instructions may be indicated to be applied to source sequence 802 in a particular order. For example, it may be possible for manipulation instructions 804 to first include a linking step and then include a mutation step. In such an example, the sequences of source sequence 802 would be linked according to the linking instructions of manipulation instructions 804 and then the linked source sequence 802 would be mutated according to the mutation instructions of the manipulation instructions 804

Similarly to communication flow 800, source sequence 802 and manipulation instructions 804 may be assigned sequence IDs and instruction IDs, respectively. Source sequence 802 and manipulation instructions 804 and their associated IDs may be received at device 808. Device 808 may then apply the manipulation instructions to the source sequence 802, utilizing the sequence IDs and the instruction IDs to ensure proper application. Applying the manipulation instructions 804 to the source sequence 802 may transform the source sequence 802 to a target sequence 810. In the example provided at FIG. 9, applying the manipulation instructions 804 to the source sequence 802 may result in multiple target sequences 810. In particular, as the manipulation instructions 804 include multiple mutation instructions for application to the source sequence 802, each of the mutation instructions is separately applied to the source sequence 802, resulting in multiple target sequences 810. Each of the target sequences 810 may also be assigned a unique sequence ID. Assigning a unique sequence ID to each of the target sequences 810 may assist in development of another target sequence. For example, in some embodiments it may be desirable to further manipulate a target sequence 810. Thus, in such examples, one or a plurality of the target sequences 810 may be utilized as a source sequence 810, and there may be manipulation instructions 804 developed for application to the target sequences 810.

Following applying manipulation instructions 804 to transform a sequence source 802 to a target sequence 810, the target sequence 810 may be transmitted to a receiving device, in some examples. The target sequence 810 may be transmitted via a network. For example, the target sequence 810 may be wirelessly transmitted to a receiving device, where the receiving device is communicatively linked to device 808. In other examples, the target sequence 810 may be transmitted to a receiving device via a hard wire connection. Once received at the receiving device, the target sequence may be displayed via a display of the receiving device. However, in some examples, the target sequence 810 may not be transmitted and may instead only be accessible directly via device 808. Thus, the target sequence may be displayed via a display of device 808.

Figure 10:
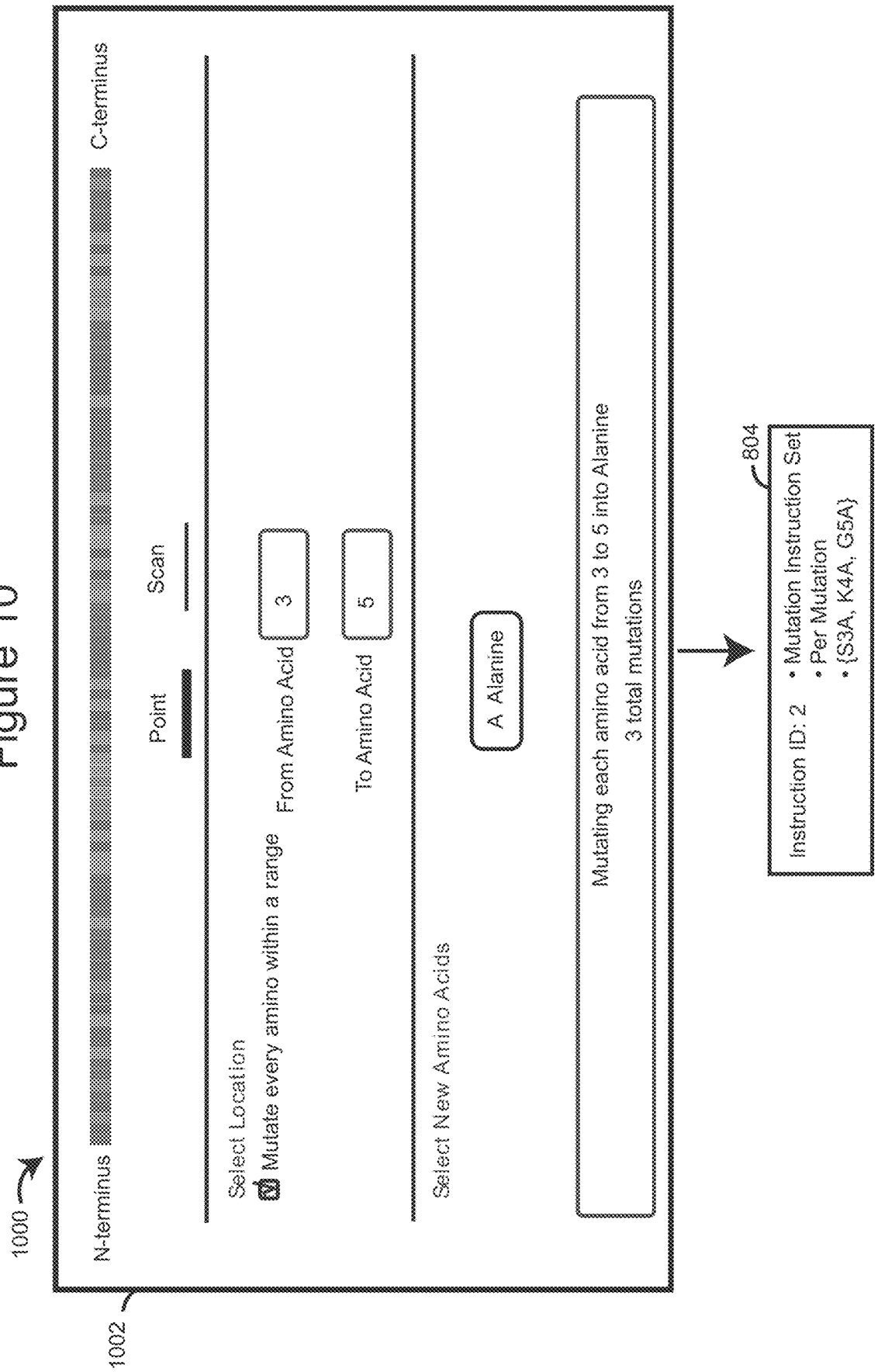
FIG. 10 shows a schematic flow diagram of an example method for obtaining manipulation instructions according to at least one example of the present disclosure.

Turning now to FIG. 10, an example flow chart of a method 1000 for determining manipulation instructions according to an embodiment of the disclosure is shown. Method 1000 may include selecting a location in a sequence for a manipulation to occur. Selecting a location in a sequence for a manipulation to occur may include selecting a position in the sequence for a manipulation to occur. In some examples, selecting a location in a sequence for a manipulation to occur may include selecting every amino acid within a range of amino acids in a sequence to be manipulated.

Following selecting a location for a manipulation to occur, method 1000 may include specifying the manipulation and a location in a sequence for a manipulation to occur at step 1002. The manipulation may include any one or combination of the biological instructions described above in reference to FIGS. 1 and 2. For example, the manipulation may be a mutation in some examples. In examples where the manipulation may be a mutation, a desired amino acid may be indicated for the mutation. Put another way, in examples where the manipulation is a mutation, the final desired amino acid after the mutation has occurred may be indicated. Examples of other manipulations include combinatorial construction of a sequence set by specifying members to be combined, construction of particular or sets of antibodies, enzymes, gene cassettes, or other sequences by means of combinatorial assembly or mutation, comparisons and specified mixings of multiple existing sequences, truncations and replacements. Following specifying the manipulation at 1002, method 1000 may include generating manipulation instructions 804. These manipulation instructions 804 may be assigned a unique instruction ID in some examples, and these manipulation instructions 804 may correspond to the manipulation instructions described in relation to the above figures. Following generating the manipulation instructions 804, method 1000 may exit.

As another example, the method and system may be understood to incorporate storage, input, and sequence transformation. As discussed herein, storage may pertain, minimally to both storage of 1) Construct Objects and Manipulation Objects. In some examples, the Construct Objects and Manipulation Objects may be stored on a single device and may be distinguished by ID, permission, database or any other method to separate the kind of object stored. There may be several types of storage. For example, two example types of sequence storage are described below. A first example type of sequence storage may be included as a part of a device for storage of a digital representation of a Construct Object. The device for storage of a digital representation of a Construct Object may include any one or combination of a separator device, a security device, and a receiving device as described above.

A digital record stored in a database on a computer that may take the form of a digitally represented genetic—amino acid or nucleic acid—construct. A record may contain a unique Construct Object ID, an amino or nucleic acid sequence, the length of the sequence, and an indication of the kind of sequence being represented. Specifically, the representation of the genetic construct may be stored as a nucleic or amino acid sequence represented by a string of letters each representing a specific nucleic or amino acid. This may include the naturally occurring 20 amino acids and 4 nucleic acids, but may also include character representations for non-naturally occurring amino acids or other encoding schemes that themselves may represent classes of the above acids.

Generally, the object may be represented by a length of amino or nucleic acids, where each amino or nucleic acid may be unknown or a placeholder for a known acid, ex. a string of "X"s of defined length.

A more complete record may also contain the calculated degraded variant sequences based on properties a user may query during the editing of the sequence, including an alternative representation of the amino or nucleic acid sequence based on, for example, the hydrophobicity, pKa, particular atoms or mass of each acid in the sequence. Additional information regarding the function, or other annotations may be included, along with administrative or technical information including checksums, deposition metadata, or biological construction rules.

A second example type of sequence storage may be included as a part of a device for storage of a digital representation of a Manipulation Object. The device for storage of a digital representation of a Construct Object may include any one or combination of a separator device, a security device, and a receiving device as described above. A digital record stored in a database on a computer may take the form of a digitally represented Manipulation Object. A minimally complete record may contain a unique Manipulation Object ID, a set of target Construct Object IDs further described as the Subject, a set of rules further described as the Verb to be applied to the target constructs, and an indication of the kind of manipulation being represented. Depending on the kind of manipulation being represented, the set of rules may be empty.

In one example, a sequence input device may be a computer or other sensor system attached to a sequence processor (e.g., a separator device, a security device, and a receiving device) that may use various input devices (e.g.— any one or more of a GUI, keyboard, mouse, microphone, camera, networking protocol, API, and other standard input device) and may be capable of interpreting a user's input as digital data which may be compatible and interpretable by other devices in this disclosure.

A single input device may be used to build the disclosure, but internal segregation through permissions may be required when the interface is used by uniquely privileged individuals or functions. An example solution may be a separate device for each permissioned category—administrator, technician, design intermediary, or manufacturer, etc.

The input device may interpret a user's input of Manipulation Data and deposit it as a Manipulation Object with a unique ID in the storage device as shown in Step 305 and 307 of FIG. 3. The device which may populate the manipulation data object may receive the above inputs in the form of any one or combination of a graphical user interface, a spoken language interface, an API, a network transmission of interpretable data, a camera which observes a user's actions or manipulations of physical objects, and other similar input mechanism. Regardless, whichever input is used however, will define a manipulation kind, a list of IDs of target Construct Objects (subject) IDs, and a list of rules (e.g., a verb) associated with the manipulation kind. Data filling these inputs may then be applied to the construct to fulfill the manipulation.

The input device may access storage devices, as shown in Step 303 of FIG. 3, restricted by permissions in order to maintain security by prevent a user's access through an input device unless they have credentialed authority to access the particular data as determined by the Administrator or other authorizing individual. Construct Object Metadata may be internally analyzed to more accurately represent a user's inputted request, or to inform the user of a likely outcome for a given manipulation. The input device may search additional databases containing compatibly formatted represented constructs, restricting results based on a property in the database: ex. by being within a particular amino acid size range, by containing particular domains, by possessing particular properties, by being deposited by particular individuals, by having a particular license, by being used in a particular publication, etc. Once a search is presented, particular results can be selected for input based on a user's preference, based on particular ranking or scoring of the results, by a user restricting the number of results by cost or number of results, or the entire set of returned results may be included.

The input device may accept natural language input in the form of written or spoken word to generate queries for a search as noted above, in some examples. Additionally or alternatively, the input device may direct a user to select features of a particular abstract or artistic representation that may be used to generate queries for the above search—for instance, selecting or pointing out physical features representing particular objects or functions, where the selection may be read into a computer which looks up constructs matching the desired physical features selected.

Multiple input devices may interact with each other, each with different permissions and capabilities, along with the storage of the Manipulation Data in order to modify the same Manipulation Data in order to build a more appropriate modification for the user, or actions to be applied to the constructs.

In a further example, the system may include a transforming processor (e.g., a computer or processing system that may compute New Construct Object Data by applying a computer function to the Construct Data already stored in a storage device. A transforming processor, which may be a transforming module of a security device in some examples, may be capable of interpreting a particular manipulation based on any one or combination of its kind, its Construct Object, and its stored rules in order to design novel genetic constructs. This transforming processor may 1) have access to data which may correlate the Construct Object IDs of the Manipulation Data with particular manufacturable sequences, and 2) may have access to software programming which may be capable of interpreting the Manipulation Data's rulesets based on the kind of manipulation being performed.

This device may produce an output called a New Construct Object in one example by accessing Sequence Data, accessing software particular to the manipulation kind, and applying the software to the given input sequence data. In the case that the construct data includes or may call actual Sequence Data, then the New Construct Object may too contain actionable and manufacturable sequence data. The transmission of the data (e.g., a target sequence, source sequence, and manipulation instructions), or parts of the data may be restricted depending on the credentials of the party receiving the transmission, or the permissions associated with the computational device, or its receivable data.

Computation may utilize any information it is permitted to retrieve for a specified manipulation, and if biological data or restrictions applicable to the assembly rules may be found for certain objects, this data may be used to inform the output. Information about the inability to be N-terminal or C-terminal in a protein, to be mixed with other particular protein domains, or inability to be expressed in particular target organisms, may all be examples of data or restrictions applicable to the assembly of certain objects.

For computation of New Construct Objects, manipulations may indicate their 'kind' to the computation device. The kind indicated to the computational device may determine the particular algorithm applied to the objects. Assembly rules within a manipulation may generally be an application of a particular operation on a mathematical 'set', including any one or combination of a Cartesian product, complements, linter section, power set, union, etc., coupled with biological assembly rules based on objects particular biological classification/organization.

In processing the rules, a database(s) (e.g., database 116) may be used to call additional data need not be the same database as the one used to assign the objects to the set. Put another way, databases called to process objects in computation of the new digital representation may not need to include the database used to identify the objects by means of the input device. For instance, a sequence database (e.g., database 116) may identify "Part 12" with a sequence "XXXXX" for population into Rule 1. For example, where upon computation, Part 12 may be called from a separate database which may include a more specific sequence of which "XXXXX" is a valid representation, but is not identical. In this way the databases may be informationally segregated and particular to a user, step in the process, regulation, or other requirement that may be placed on the storage and transmission of data. This sharing of the identity of "Part 12" across a number of different databases may permit different administration of segregated databases for particular, exclusive, purposes for example, databases owned and operated by a particular pharmaceutical company with proprietary information, a DNA synthesizer with particular proprietary information, a design company with particular proprietary information, and a customer with particular sensitive information. And in this way multiple users with different information security requirements (and different purposes for possessing particular information) may communicate with each other about the same object without compromising their particular requirements for data protection.

For example, the manipulation record may lack the actual sequence data of the subject construct upon which the manipulation is to be performed. Different parties may host servers or computers capable of storing and transmitting data regarding the manipulations and the constructs for particularly credentialed requests. A sequence computing device (e.g., separator device, security device, and receiving device) may serve multiple roles—as a storage, input, or sequence transforming device, if is appropriate for the particular permissioned architecture.

The sequence computing device may be capable of reconstructing data for various purposes, and may be appropriately credentialed to access different amounts of data used to fulfill its purpose. Were a manufacturer of genetic material to have control over the device, it may be credentialed to call and subsequently calculate genetic sequences, but lack the credentials to query data sufficient to calculate ancillary biological data about the resulting genetic constructs. Were a genetic design intermediary to have control over the calculation device, it may be credentialed to call and subsequently calculate the properties, capabilities, functions and limitations of the products it is instructed to produce, but would lack the credentials to query the actual genetic sequence of the subject or product of its operations. Given the granular and credentialed nature of the transmission, any number of parties may take ownership of the sequence transformer.

The sequence computing devices may be multiple and separate, each under the control of various parties involved in the design and production of a construct. The sequence computing devices may all be identical in functionality aside from their credentials, or they may have particular functionalities restricted or augmented based on their credentials. Regardless, they may apply consistent sequence processor programming to calculate output products from their given input data and rulesets to be applied to the input data.

The sequence computing devices used for inputting a user's data may be multiple and spread out physically, and need only be, at some point, capable of communicating. For example, the sequence computing devices may communicate via any one or combination of network transmission, reading of physical media, and otherwise reading the data, regarding the input of their user to the storage of manipulation or construct data.

As discussed above, three kinds of devices—storage, input and a sequence transformer—and multiple iterations of them may be separable in both space and privilege, permitting multiple parties to engage in work regarding the genetic constructs without necessitating full-knowledge of the sequences involved. Further, segregation may permit any given sequence computing device to be swapped out, or have redundant, or multiple versions of itself on the same network. Distributing each sequence computing device within the same disclosure and allowing for multiple versions of each component permits even further distribution and parsing of knowledge as it passes through the disclosure, and may permit even more parties, physical segregation of data, and different representations of the same data.

The disclosure may enable multiple parties to communicate and manipulate information about genetic constructs relevant to their efforts without necessitating any single party possess full knowledge of the constructs and manipulations involved. This may be accomplished by transmitting instructions for manipulation along with an identifier of the subject constructs of the manipulation, rather than calculating manipulations on a subject directly and transmitting the results of that calculation. By calculating the product of a manipulation (e.g., a target sequence) on devices separable by possession or privilege, the initial sequences as well as the ultimate sequences produced may be calculated in an environment independent and outside of the control of those suggesting or aiding the design of a particular manipulation.

The segregation of devices additionally ensures that those conducting the manipulation may possess only enough information about the constructs to engage productively, but not sufficient information to determine the underlying sequence of their manipulation. Further, the final calculation device may itself only possess sufficient information in order to perform the calculation of a new construct, and may not have access to particular information regarding how a technician arrived at a particular manipulation. In this way, each node of a multi-party system may maintain independent control over information, only passing required information to each other party—while enabling the construction, storage and manufacture of a genetic construct (i.e., target sequence), all without any node having full access to all information in the system. A practical implementation of the present disclosure may involve the deposition, editing, verification and production of a novel genetic construct by four different levels of permission, each having only sufficient data minimally required for a given privileged party's role in the submission, design, organization, and manufacture of the genetic constructs.

Although the structure may in one example be understood as distinct physical devices, it may also be effective as a single sequence computing device segregating functions and access through varying levels of permissions. For instance, one example implementation of the disclosure may include the following: 1) an administrator of a scientific project would use the input device to input a nucleic or amino acid as a basic Construct Object, for which a unique ID is generated. Access to that object may be protected by varying degrees of predefined privileges in the construct storage device. 2) A technician may then use a similar, yet differently permissioned, input device to query that unique ID, populating it further with functional information along with various descriptive data. Additionally, that technician may input a Manipulation Object containing Manipulation Data, describing changes to be made to the construct object which was inputted by the administrator as Sequence Data. The input device used by the technician may translate their suggested manipulations into computer-readable Manipulation Data, which may be applied to a particular Construct Object. A Manipulation Object created by the technician at this stage may be executed without him/her actually requiring access to the sequence or other data submitted by the administrator. 3) A design intermediary, who may be a consultant, purveyor of the disclosure itself, or some other entity, may additionally access data submitted by the scientist—metadata derived from the sequence and annotation metadata—and may even input additional annotation metadata in order to better guide the manufacturer's assembly of the genetic objects. The design intermediary may adjust, inform, price, diagnose issues, make annotations, or otherwise provide additional information about the design process using information to which it may be uniquely privy—with or without revealing that information to the technician, administrator or manufacturer. 4) Finally, a manufacturer of genetic material may receive a request to produce the newly-computed construct object sequence, which was computed by applying manipulation data to the original construct object sequence data. In the act of production, the manufacturer must know the sequences to be produced, and thus must either have access to the newly-computed construct object sequence or the device performing the computation. The manufacturer, however, may lack access to data beyond the sequences to be produced.

In this way, four parties may be engaged in the design, communication and production of new biological constructs without any single party having full access to actionable data.

Segregating privileged information keeps to a minimum the transmission of a confidential sequence of interest (i.e., target sequence), of functional proprietary data, and of logistical data relevant for design; permitting the senior scientist to protect sequence information, the technician to protect experimental data, the design company to protect design requirements, and the manufacturer to protect manufacturing principles, all while being able to design, price, deliver and execute an order for specific sequences.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A sequence security system, comprising:
a security device communicatively coupled to a separator module, the separator module comprising a first separator device and a second separator device, and the security device storing instructions in non-transitory memory that are executable by a processor to:
receive a source sequence transmitted from the first separator device at a receiving module, wherein the source sequence received is a construct object comprising a sequence without manipulation instructions applied thereto,
separately receive the manipulation instructions from the second separator device at the receiving module, where the manipulation instructions received are usable to transform the source sequence into a confidential target sequence, the source sequence and the manipulation instructions maintained separate from one another until the source sequence and the manipulation instructions are received at the receiving module, then
apply the manipulation instructions to the source sequence to transform the source sequence into the confidential target sequence via a transforming module, wherein the confidential target sequence is a new construct object, and then
send the confidential target sequence to a receiving device,
wherein the receiving device receives the confidential target sequence, and
wherein the receiving device lacks access to data for the source sequence and the manipulation instructions.

2. The system of claim 1, wherein the confidential target sequence is sent to the receiving device via a transmitting module, wherein the source sequence received is an untransformed construct object, and wherein the confidential target sequence is a transformed confidential target sequence.

3. The system of claim 2, wherein the confidential target sequence is encrypted at the transmitting module prior to being transmitted to the receiving device, and wherein the confidential target sequence is a genetic construct.

4. The system of claim 1, wherein the source sequence encodes a protein.

5. The system of claim 1, wherein the manipulation instructions are translated from plain language prior to being received at the receiving module.

6. The system of claim 1, wherein the first device comprises a first user input device, and wherein the first device has a first permission level that allows the first device to access the source sequence and prevents the first device from accessing the manipulation instructions and the confidential target sequence, and
wherein the second device comprises a second user input device, and wherein the second device has a second permission level that allows the second device to access the manipulation instructions prevents the second device from accessing the source sequence and the confidential target sequence.

7. A method, comprising:
separately receiving a source sequence from a first device and manipulation instructions from a second device, wherein the source sequence is an unaltered sequence; then
transforming the source sequence into a confidential target sequence by applying the manipulation instructions to alter the source sequence via a security device, wherein the confidential target sequence is different than the unaltered sequence; and
transmitting the confidential target sequence,
wherein the first device has a first permission level that allows the first device to access the source sequence and prevents the first device from accessing the manipulation instructions and the target sequence, and
wherein the second device has a second permission level that allows the second device to access the manipulation instructions prevents the second device from accessing the source sequence and the target sequence.

8. The method of claim 7, wherein applying the manipulation instructions includes querying a database to determine operations to apply the manipulation instructions to the source sequence.

9. The method of claim 7, wherein the confidential target sequence is transmitted to a receiving device, wherein the receiving device receives the confidential target sequence, and wherein the receiving device lacks access to data for the source sequence and the manipulation instructions.

10. The method of claim 7, wherein the source sequence is received as a first information packet, and wherein the manipulation instructions are received as a second information packet.

11. The method of claim 10, wherein the first information packet and the second information packet are maintained separate from one another until the first information packet and the second information packet are both received at the security device.

12. The method of claim 7, further comprising interpreting the manipulation instructions by accessing a database prior to applying the manipulation instructions to the source sequence.

13. The method of claim 12, wherein the confidential target sequence is transmitted to a receiving device, the method further comprising successfully verifying that the receiving device has a permission level that permits display of the confidential target sequence prior to transmitting the confidential target sequence to the receiving device.

14. The method of claim 7, wherein the manipulation instructions are originally received as plain language and automatically translated from the plain language to the manipulation instructions, wherein the plain language is a form that is unusable by the security device, and wherein the manipulation instructions are in a form that is usable by the security device.

15. A method, comprising:
receiving user generated instructions that include plain language via a user input, wherein the plain language is unable to be executed via a processor of a security device;
translating the plain language to manipulation instructions that are executable via the processor of the security device;
transmitting the manipulation instructions to the security device;
applying the manipulation instructions to a source sequence via the security device to form a target sequence, wherein the manipulation instructions and the source sequence are transmitted to the security device via separate information packets; and
displaying the target sequence,
wherein the target sequence is different than the source sequence,
wherein the first device has a first permission level that allows the first device to access the source sequence and prevents the first device from accessing the manipulation instructions and the target sequence, and wherein the second device has a second permission level that allows the second device to access the manipulation instructions prevents the second device from accessing the source sequence and the target sequence.

16. The method of claim 15, further comprising transmitting the target sequence to a receiving device, and displaying the target sequence via the receiving device.

17. The method of claim 16, wherein a first verification step successfully verifies that the receiving device has a permission level that allows viewing of the target sequence before transmitting the target sequence to the receiving device, and wherein a second verification step verifies that a user has permission to view the target sequence prior to displaying the target sequence.

18. The method of claim 16, wherein the receiving device receives the confidential target sequence, and wherein the receiving device lacks access to data for the source sequence and the manipulation instructions.

19. The method of claim 15, wherein the manipulation instructions are received at the security device via a first information packet, and wherein the source sequence is received at the security device via a second information packet.

20. The method of claim 15, wherein the plain language received via the user input includes technical terms that are indicative of manipulation instructions.

\* \* \* \* \*